US009486770B2

(12) United States Patent
Trau

(10) Patent No.: US 9,486,770 B2
(45) Date of Patent: Nov. 8, 2016

(54) COMBINATORIC ENCODING METHODS FOR MICROARRAYS

(71) Applicant: NATIONAL UNIVERSITY OF SINGAPORE, Singapore (SG)

(72) Inventor: Dieter Trau, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 14/409,511

(22) PCT Filed: Jul. 19, 2013

(86) PCT No.: PCT/SG2013/000301
§ 371 (c)(1),
(2) Date: Dec. 19, 2014

(87) PCT Pub. No.: WO2014/014422
PCT Pub. Date: Jan. 23, 2014

(65) Prior Publication Data

US 2015/0182932 A1 Jul. 2, 2015

(30) Foreign Application Priority Data

Jul. 20, 2012 (GB) .................................. 1212902.9

(51) Int. Cl.
*C40B 50/16* (2006.01)
*B01J 19/00* (2006.01)
(Continued)

(52) U.S. Cl.
CPC .......... *B01J 19/0046* (2013.01); *C12Q 1/6834* (2013.01); *C12Q 1/6837* (2013.01); *C40B 50/16* (2013.01); *G01N 33/6803* (2013.01); *B01J 2219/005* (2013.01); *B01J 2219/0054* (2013.01); *B01J 2219/0074* (2013.01); *B01J 2219/00466* (2013.01); *B01J 2219/00648* (2013.01); *B01J 2219/00659* (2013.01); *B01J 2219/00702* (2013.01); *B01J 2219/00722* (2013.01); *C40B 20/02* (2013.01)

(58) Field of Classification Search
None
See application file for complete search history.

(56) References Cited

U.S. PATENT DOCUMENTS 8,927,465 B2 * 1/2015 Trau ..................... B01J 19/0046 382/128
2003/0073086 A1 4/2003 Guire et al.
(Continued)

FOREIGN PATENT DOCUMENTS

WO WO 0120593 A1 3/2001
WO WO 2008016335 A1 2/2008
(Continued)

*Primary Examiner* — Samuel Woolwine
*Assistant Examiner* — Kaijiang Zhang
(74) *Attorney, Agent, or Firm* — Leydig, Voit & Mayer, Ltd.

(57) ABSTRACT

A method of encoding a microarray includes depositing a first batch of particles on a substrate. The first batch of particles comprises a mixture of at least two sub-batches of the particles. Each of the sub-batches is capable of binding to a different, specific target analyte. Information necessary for decoding the microarray is provided prior to or during the depositing and includes a unique particle number ratio of the sub-batches. If more than one batch of particles is deposited, an image can be taken of the first batch prior to depositing subsequent batches to provide information about the position of the particles in the first batch of particles. These depositing and imaging steps can be sequentially repeated for the subsequent batches. Such a microarray having multiple batches can be decoded using the information about the position of the particles and the known particle number ratios of the sub-batches.

32 Claims, 9 Drawing Sheets

(51) Int. Cl.
*C12Q 1/68* (2006.01)
*G01N 33/68* (2006.01)
*C40B 20/02* (2006.01)

(56) References Cited

U.S. PATENT DOCUMENTS

2003/0148544 A1* 8/2003 Nie et al. ............... B82Y 15/00
436/524
2004/0132122 A1* 7/2004 Banerjee et al. .... B01J 19/0046
435/7.92
2010/0075865 A1* 3/2010 Trau et al. ......................... 506/9

FOREIGN PATENT DOCUMENTS

WO WO 2010003132 A1 1/2010
WO WO 2011127042 A1 10/2011

* cited by examiner

Relative bead signal intensity

Bead count

Total number of beads deposited on substrate

Bead number ratio of 1 : 2 : 4 : 8

Sub-batch 1 (24 beads)

Sub-batch 2 (3 beads)

Sub-batch 3 (12 beads)

Sub-batch 4 (6 beads)

Bead signal intensity

COMBINATORIC ENCODING METHODS FOR MICROARRAYS

CROSS-REFERENCE TO PRIOR APPLICATIONS

This application is a U.S. National Stage Application under 35 U.S.C. §371 of International Application No. PCT/SG2013/000301 filed on Jul. 19, 2013 and claims benefit to British Patent Application No. GB 1212902.9 filed on Jul. 20, 2012. The International Application was published in English on Jan. 23, 2014 as WO 2014/014422 A1 under PCT Article 21(2). The contents of the priority British Patent Application No. GB 1212902.9 is hereby incorporated by reference in its entirety for all purposes.

FIELD

The present invention generally relates to a process for encoding and decoding a microarray. The present invention also relates to a microarray.

BACKGROUND

Microarrays are important tools for diagnostic applications in research and clinical settings. A major process in the fabrication of microarrays is the patterning of biomolecules such as proteins and DNA onto a solid support in a controlled fashion. In traditional microarrays, biomolecules such as proteins and DNA are introduced directly onto a solid substrate surface using spotting technology. However, the poor precision and low reproducibility of spotting technology results in the production of microarrays with numerous inaccuracies.

On the other hand, bead microarrays carry microbeads which in turn are conjugated to biomolecules. Bead microarrays have significant advantages over traditional spotted microarrays, such as consistency, flexibility and faster kinetics. Bead microarrays offer greater flexibility because the surface chemistry of the beads can be tailored to suit the biomolecule to be conjugated on the bead. Potentially, any type of microarray such as drug-, metabolite-, lipid- or carbohydrate-microarrays can be manufactured by using beads. Further, bead microarrays ensure consistent results since the dimensions of the beads can be made identical.

However, one of the main problems with bead microarrays is the encoding and decoding of individual beads to determine the identity of the bead and the type of molecule the bead carries.

Currently, bead arrays typically come in the form of “liquid arrays” or “planar arrays”. In liquid arrays, beads remain in suspension and are read out and decoded via a physical signature, e.g a color tag, during flow cytometer based analysis, such as VERACODE assays of ILLUMINA INC., San Diego, Calif., United States of America and XMAP referencing of LUMINEX CORPORATION of Austin, Tex., United States of America.

In planar arrays, beads are deposited onto a substrate material and typically identified by a physical signature, e.g. color tags, oligonucleotide sequences, bead shape and size or other means. The array is analyzed by taking a picture, typically with a microscope or microarray scanner.

SUMMARY

In an embodiment, the present invention provides a microarray for detecting a presence of one or more target analytes in a sample. An array of particles comprises one or more binding sites thereon for binding with the one or more target analytes present in the sample. The array of particles has at least two particle subsets. Each of the subsets has at least one binding site to one or more of the target analytes that are unique to the respective subset. A number of particles of each of the subsets is known and the known number of particles of each of the subsets is useable to generate a ratio value of particle subsets such that a presence of two or more of the target analytes in the sample is thereby detectable.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
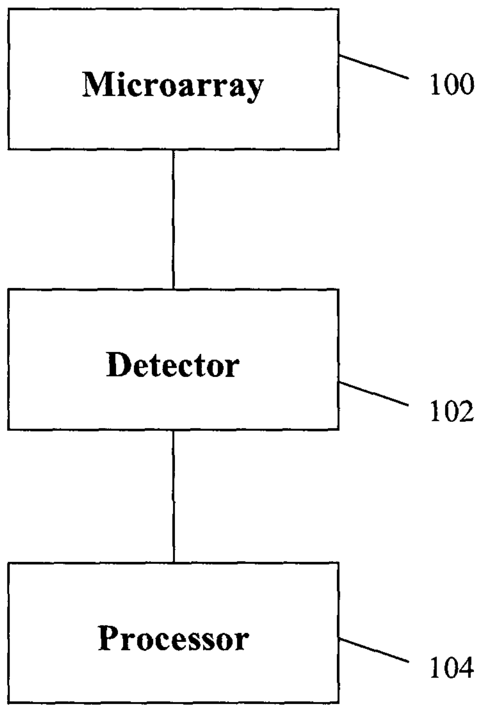
FIG. 1 is a schematic diagram showing components of a system according to an embodiment of the present invention.

The present invention recognizes that both approaches of the prior art described above suffer from the need for a physical tag for each microbead in order to distinguish between different populations of beads carrying different functional molecules on their surface. The creation of different tags or libraries of tags with a desired size of 1000 to 100000 different tags is complicated and to date has only been partly solved. Currently, libraries with a maximum number of about 500 tags are commercially available. In addition, the use of tags adds to the complexity and cost of manufacturing the microarray. Tags may also interfere with the analyte binding and subsequently the readout of the bead.

Therefore, the present invention recognizes a need to provide an encoding and decoding method for microarrays that do not require tags that overcomes, or at least ameliorates, one or more of the disadvantages described above.

The present invention also recognizes a need to provide a microarray that overcomes, or at least ameliorates, one or more of the disadvantages described above.

According to a first embodiment, there is provided a method of encoding a microarray. The method comprises a) depositing at least one batch of particles on a substrate of a microarray, wherein each batch of particles comprises at least two sub-batches of particles and wherein in case more than one batch of particles is deposited each batch of particles is deposited separately and an image is taken of each batch of particles on the microarray after deposition to identify the position of the particles of each batch on the microarray, wherein (i) in case only one batch of particles is deposited the number of particles of each sub-batch is unique to that sub-batch of particles resulting in a unique particle number ratio for the one batch; or (ii) in case at least two batches of particles are deposited the particle number ratio for each batch is either the same or different from each other; wherein each sub-batch of particles deposited on the microarray is capable of binding to a specific target-analyte, wherein each sub-batch of a batch binds to a different target-analyte compared to all other sub-batches of the respective batch; and b) recording information about the position of particles of the batch(es) and information of the particle number ratio for the batch(es) obtained under a) for each microarray produced according to this method; wherein the position of the particles and the particle number ratio within a batch allows determining which target analyte is present in a test sample to be analyzed with the microarray or in case only one batch is deposited the particle number ratio of the batch allows determining which target analyte is present in a test sample to be analyzed with the microarray.

According to a second embodiment, the present invention provides a method of decoding a microarray obtained via a method referred to above. The method comprising a. analyzing an image obtained from an entity which conducted a screening test using a microarray as referred to in claim 1; wherein analyzing of the image comprises: (i) determining the position and number or intensity of detectable signals obtained from binding of the target analyte to a particle deposited on the microarray; and (ii) decoding the information obtained under (i) by comparing the information obtained under (i) with the information recorded in step b) of claim 1 to identify the target analyte bound to the particles of the microarray.

According to a third embodiment the present invention provides a microarray for detecting the presence of one or more target analytes in a sample, the microarray comprising:

an array of particles having one or more binding sites thereon for binding with said one or more target analytes present in the sample, wherein the particle array comprises at least two particle subsets, each subset having at least one binding site to one or more target analytes that are unique to that subset and wherein the number of particles of each subset is known and the known number of particles of each subset is used to generate a ratio value of particle subsets to detect the presence of two or more target analytes in a sample.

In one embodiment, there is provided a microarray as described herein, wherein the ratio value is between 100/1 and 1/1.

In another embodiment, there is provided a microarray as defined herein, wherein the ratio value is between 11/1 and 1/1.

In one embodiment, there is provided a microarray as defined herein, wherein the ratio value is a prime number.

In another embodiment, there is provided a microarray as defined herein, wherein the known number of particles of each subset is unique to that subset.

In one embodiment, there is provided a microarray as defined herein, wherein each particle emits a change in a detectable signal when a target analyte binds to at least one of the binding sites of the particle.

In one embodiment, there is provided a microarray as defined herein, wherein the change in the detectable signal of the particles is an optical signal.

In one embodiment, there is provided a microarray as defined herein, wherein the binding sites of the particles of one subset bind to only one target analyte.

In one embodiment, there is provided a microarray as defined herein, wherein the particles are selected from the group consisting of microbeads and biological entities.

In one embodiment, there is provided a microarray as defined herein, wherein the microbeads have a shape selected from the group consisting of microsphere, microcapsule, microrod, microcube and microtube.

In one embodiment, there is provided a microarray as defined herein, wherein the microbeads are formed of a material selected from the group consisting of plastic, ceramic, glass, metal, a metal oxide, silicon dioxide, polystyrene, methylstyrene, acrylic polymer, sepharose, cellulose, nylon, cross-linked micelles, Teflon, paramagnetic material, thoria sol, carbon graphite, titanium dioxide, latex, a cross-linked dextran, and compositions used in peptide, nucleic acid and organic moiety synthesis or mixtures thereof such as a metal filled polymer particle.

In one embodiment, there is provided a microarray as defined herein wherein the biological entities are selected from the group consisting of a cell, a bacterium, or a virus particle.

In one embodiment, there is provided a microarray as defined herein, wherein the particles are of a size of 0.1 to 500 μm, or 0.1 to 200 μm, or 0.1 μm to 100 μm, or 1 to 100 μm, or 1 to 10 μm.

In one embodiment, there is provided a microarray as defined herein, wherein each particle comprises one or more active agents capable of binding with one or more target analytes.

In one embodiment, there is provided a microarray as defined herein, wherein the number of binding sites of the one or more active agents on each particle is known and is used to generate a ratio value of binding sites to indicate the presence of two or more target analytes.

In a further embodiment, there is provided a microarray as defined herein, wherein the particles comprise at least two active agents that are capable of detecting at least two target analytes and wherein the number of binding sites on each particle is known and is used to generate a ratio value of binding sites to indicate the presence of two or more target analytes in a sample.

In another embodiment, there is a provided a microarray as defined herein, wherein the active agent is a chemical or bioactive agent.

In yet another embodiment, there is provided a microarray as defined herein, wherein the active agent is selected from the group consisting of peptides, proteins, nucleic acids, metabolites, carbohydrates, enzymes, antibodies, hormones, lectines, drugs, pesticides, allergens, antigens, receptors, fatty acids, oligopeptides, small organic molecules, coordination complexes, aptamers, cells, cell fragments, virus particles, polysaccharides, polynucleotides, lipids and mixtures thereof.

In one embodiment, there is provided a microarray as defined herein, wherein the particles are tagged with an identifier.

In another embodiment there is provided a microarray as defined herein, wherein the identifier is selected from the group consisting of a fluorescent tag, a bar code, a chemical identifier, a quantum dot, a microstructure, a nucleic acid identifier, an engraving and a radio frequency tag.

In a fourth embodiment, there is provided a system for determining the presence of one or more target analytes in a sample, the system comprising:

a microarray having an array of particles having one or more binding sites thereon for binding with said one or more target analytes present in the sample, wherein the particle array comprises at least two particle subsets, each subset having at least one common binding site to one or more target analytes that are unique to that subset and wherein the number of particles of each subset is known and the known number of particles of each subset is used to generate a ratio value of particle subsets to indicate the presence of two or more target analytes in the sample;

a detector configured in use to detect the change in the detectable signal emitted by the particles;

a processor configured in use to count the number of particles that emit a change in a detectable signal based on the detected change in the detectable signal to determine the presence or absence of one or more target analytes that are unique to said particle subsets.

In one embodiment, there is provided a system as defined herein, further comprising:

an imager configured in use to image the microarray;

a memory configured in use to record the location of each particle based on the images obtained from the imager; and wherein the processor is configured in use to interrogate the memory and compare the recorded location of each particle with the data received from the detector to identify the presence or absence of one or more target analytes that are unique to the particle subsets.

In a further embodiment, there is provided a system as defined herein, wherein each particle emits a change in a detectable signal when a target analyte binds to at least one of the binding sites of the particle.

In another embodiment, there is provided a system as defined herein, wherein the change in the detectable signal of the particles is an optical signal.

In another embodiment, there is provided a system as defined herein, wherein the detector is an optical detector.

In one embodiment, there is provided a system as defined herein, wherein the ratio value is between 100/1 and 1/1.

In another embodiment, there is provided a system as defined herein, wherein the ratio value is between 11/1 and 1/1.

In another embodiment, there is provided a system as defined herein, wherein the ratio value is a primer number.

In yet another embodiment, there is provided a system as defined herein, wherein the known number of particles of each subset is unique to that subset.

In another embodiment, there is provided a system as defined herein, wherein the binding sites of the particles of one subset bind to only one target analyte.

In another embodiment, there is provided a system as defined herein, wherein each particle comprises one or more active agents capable of binding with one or more target analytes.

In a further embodiment, there is provided a system as defined herein, wherein the number of binding sites of the one or more active agents on each particle is known and is used to generate a ratio value of binding sites to indicate the presence of two or more target analytes.

In a further embodiment, there is provided a system as defined herein, wherein the particles comprise at least two active agents that are capable of detecting at least two target analytes and wherein the number of binding sites of the active agents on each particle is known and is used to generate a ratio value of binding sites to indicate the presence of two or more target analytes in the sample.

The further features stated above in respect of the first to third embodiments are equally applicable and hereby restated in respect of the fourth embodiment.

In a fifth embodiment, there is provided a method of manufacturing a microarray comprising the steps of:

i) providing at least two subsets of particles having one or more binding sites thereon for binding with one or more target analytes present in a sample, ii) preparing a mixture of at least two subsets of particles wherein the number of particles of each subset is known and the known number of particles of each subset is used to generate a ratio value of particle subsets to indicate the presence of two or more target analytes in a sample, iii) depositing the mixture of particle subsets onto a substrate to form a microarray.

In one embodiment, there is provided a method as described herein, further comprising the step of imaging the substrate having the particles deposited thereon.

In another embodiment, there is provided a method as defined herein, further comprising sequentially repeating the steps as defined above.

In another embodiment, there is provided a method as defined herein, wherein the ratio value is between 100/1 and 1/1.

In another embodiment, there is provided a method as defined herein, wherein the ratio value is between 11/1 and 1/1.

In yet another embodiment, there is provided a method as defined herein, wherein the ratio value is a prime number.

In another embodiment, there is provided a method as defined herein, wherein the known number of particles of each subset is unique to that subset.

In yet another embodiment, there is provided a method as defined herein, wherein the known number of particles of each subset is unique to that subset.

In another embodiment, there is provided a method as defined herein, wherein the binding sites of the particles of one subset bind to only one target analyte.

In another embodiment, there is provided a method as defined herein, wherein each particle comprises one or more active agents capable of binding with one or more target analytes.

In a further embodiment, there is provided a method as defined herein, wherein the number of binding sites of the one or more active agents on each particle is known and is used to generate a ratio value of binding sites to indicate the presence of two or more target analytes.

In yet another embodiment, there is provided a method as defined herein, wherein the particles comprise at least two active agents that are capable of detecting at least two target analytes and the number of binding sites on each particle is known and is used to generate a ratio value of binding sites to indicate the presence of two or more target analytes in a sample.

In one embodiment, there is provided a method as defined herein, wherein the substrate is selected from the group consisting of polymeric materials, organic materials, inorganic materials, metals, ceramics, plastic, rubber, glass, fibrous materials, graphite or silicon, silicon dioxide, silicon nitride, modified silicon, glass, modified or functionalized glass, inorganic glass, plastics, acrylics, polystyrene, copolymers of styrene, polypropylene, polyethylene, polybutylene, polyurethane, Teflon, polysaccharide, nylon, nitrocellulose, resins, silica, silica-based materials and carbon.

The further features stated above in respect of the first to fourth embodiments are equally applicable and hereby restated in respect of the fifth embodiment.

In a sixth embodiment, there is provided a method for determining the presence of one or more target analytes in a sample, the method comprising the steps of:

contacting the sample with an array of particles having one or more binding sites thereon for binding with said one or more target analytes present in the sample, the particles emitting a change in a detectable signal when a target analyte binds to at least one of the binding sites of the particles, wherein the particle array comprises at least two particle subsets, each subset having at least one binding site to one or more target analytes that are unique to that subset and wherein the number of particles of each subset is known;

detecting the change in the detectable signal emitted by the particles; and counting the number of particles that emit a change in a detectable signal based on the detected change in the detectable signal to determine the presence or absence of one or more target analytes that are unique to said particle subsets.

In a further embodiment, there is provided a method as defined herein, further comprising the steps of:

detecting the magnitude of the change in the detectable signal emitted by the particles; and determining the number of binding sites that have bound to a target analyte based on the change in detectable signal to determine the presence or absence of one or more target analytes that are unique to the particle subsets.

In one embodiment, there is provided a method as defined herein, further comprising the steps of:

imaging the microarray;

recording the location of each particle based on the images obtained; and comparing the detected change in the detectable signal with the recorded location of each particle to identify the presence or absence of one or more target analytes that are unique to the particle subsets.

In one embodiment, there is provided a method as defined herein, further comprising the step of:

contacting the particles with a reagent to identify the presence or absence of one or more target analytes that are unique to the particle subsets on the basis that the particle subsets emit a change in detectable signal only when contacted with that particular reagent.

In another embodiment, there is provided a method as defined herein, wherein the reagent is a fluorescently labeled binding molecule, or an antibody, or a receptor, or an aptamer.

In one embodiment, there is provided a method as defined herein, wherein the detectable signal is an optical signal.

In one embodiment, there is provided a method as defined herein, wherein the target analyte is an inorganic or organic molecule.

In another embodiment, there is provided a method as defined herein, wherein the target analyte is selected from the group consisting of an environmental pollutant, a chemical, a biomolecule, a whole cell, a bacteria, a virus and a spore.

In one embodiment, there is provided a method as defined herein, wherein the environmental pollutant is selected from the group consisting of pesticides, insecticides and toxins.

In one embodiment, there is provided a method as defined herein, wherein the chemical is selected from the group consisting of solvents, polymers and organic materials.

In one embodiment, there is provided a method as defined herein, wherein the biomolecule is selected from the group consisting of hormones, cytokines, proteins, nucleic acids, lipids, allergens, carbohydrates, enzymes, antibodies, antigens, cellular membrane antigens and receptors or their ligands.

In one embodiment, there is provided a method as defined herein, wherein the whole cell is selected from the group consisting of eukaryotic cells, prokaryotic cells, mammalian cells, tumour cells, blood cells, epithelial cells, nerve cells and muscle cells.

In one embodiment, there is provided a method as defined herein, wherein the virus is selected from the group consisting of retroviruses, herpesviruses, adenoviruses and lentiviruses.

In one embodiment, there is provided a method as defined herein, wherein an identifier is added to the target analyte.

In another embodiment, there is provided a method as defined herein, wherein the identifier is selected from the group consisting of a fluorescent tag, a bar code, a chemical identifier, a quantum dot, a microstructure, a nucleic acid identifier, an engraving and a radio frequency tag.

In yet another embodiment, there is provided a method as defined herein, wherein the identifier is directly conjugated to the target analyte or indirectly conjugated to the target analyte by means of a linker molecule.

The further features stated above in respect of the first to fifth aspect are equally applicable and hereby restated in respect of the sixth aspect. Also, the further features stated above in respect of the sixth aspect are equally applicable and hereby restated in respect of the first to third aspects.

Definitions

The following words and terms used herein shall have the meaning indicated:

The terms "combinatory encoding" or "combination encoding" as used herein refers to the disclosed microarray encoding and decoding process.

The terms "microarray" or "array" as used herein refers to an array of particles on a solid support, wherein each particle has a selected, active agent capable of binding with a specific target analyte. In other examples the active agent is capable of binding with more than one target analyte.

The term "particle" refers to nano- or microparticles. In one example a particle has a particle size in the micron-sized range, or from 0.1 microns to about 1000 microns or from 1 micron to 500 microns. In one embodiment, when the particle is substantially spherical in shape, the particle size refers to the diameter of the particle, which is in the micron-sized range. Where the particle is spherical shaped, the "particle" is then termed as a "bead", such as a nonobead or microbead. In another embodiment where the particle does not have a spherical shape, the particle size may refer to the equivalent diameter of the particle relative to a spherical particle or may refer to a dimension (length, breadth, height or thickness) of the non-spherical particle.

The term "sub-batch" or "subset" as used herein, refers to particles of the same kind and carrying the same biorecognition molecule or "active agent" on its surface. Beads of a sub-batch or subset are identical with one another and bind to the same target analyte via the active agent on their surface.

The term "batch" as used herein refers to a plurality of particles formed from two or more sub-batches. The bead number ratio or ratio value of the sub-batches can be equal and/or different.

The term "super-batch" as used herein refers to plurality of particles formed from two or more batches. The bead number ratio or ratio value of the batches can be equal and/or different.

The term "population" as used herein refers to the total collection of particles deposited on a microarray.

The term "plurality of particles" as used herein refers to any number of particles greater than 1; typically a large number of particles.

The term "known" refers to a fixed or predetermined number. For example, the number of particles in a subset may be fixed or predetermined or the number of binding sites on each particle may be fixed or predetermined.

The term "encoding" as used herein refers to the identification of microbeads in a sub-batch, batch or super-batch to determine the "active agent" carried by the microbead or the analyte detected by the microbead.

The terms "lockingly engaged" or grammatical variants thereof refers to the stable deposition of the bead onto the surface; wherein the bead will keep its spatial position on the substrate during the deposition of further beads and the performance of bioassays.

The term "active agent" refers to any chemical agent that is chemically active or biological agent that is biologically active and which is capable of binding or reacting with a target analyte or an intermediary bound to the target analyte. The active agent may exhibit chemical activity and may include an environmental contaminant such as organic materials (for example, aliphatic hydrocarbon compounds, aromatic-containing compounds and chlorinated compounds) or inorganic materials (for example, metals and nitrates); a chemical warfare agent (for example, nerve agents such as sarin, soman, tabun and cyclosarin, blood agents such as arsines and hydrogen cyanide, or lachrymatory agents such as tear gas and pepper spray); a herbicide; a pesticide; a metabolite; a drug; lipids, carbohydrates, or a chemical catalyst. The active agent may exhibit biological activity and may be referred to in the specification as a "bioactive agent".

Exemplary bioactive agents include proteins, antibodies, oligopeptides, small organic molecules, coordination complexes, aptamers, cells, cell fragments, virus particles, antigens, polysaccharides, lipids and polynucleotides, which can be attached to or bonded to a particle. Accordingly, the term "biologically active particle" refers to a particle as defined herein which has an active agent that has biological activity or by itself is biologically active.

The term "chemical active particle" refers to a particle as defined above which has an active agent that has a chemical activity. The term "active agent" may also refer to an agent exhibiting physical activity, such as responding to a physical stimulus in a predetermined way including processes such as emission of light upon excitation, emission of heat upon absorption of electromagnetic radiation or microwaves.

The term "target analyte" refers to a substance to be detected that is capable of binding to the active agent. A target analyte may also be a substance to be detected for calibration purposes. Exemplary target analytes include, but are not limited to, nucleic acids, polynucleotides, drugs, hormones, proteins, enzymes, antibodies, carbohydrates, receptors, bacteria, cells, virus particles, spores, lipids, allergens and antigens. The target analytes may be directly or indirectly labeled with a tag to generate a signal. Typically but not limiting tags are fluorescent tags, dyes, quantum dots, particles, enzymes, electrochemical active compounds or other signal generation entities.

The term "specific binding substance" may refer to a substance which has a specific affinity for a certain substance. For example, a target analyte in a sample may be capable of undergoing a specific binding reaction with the active agent. Examples of combinations of the specific substance with the specific binding substance include: antigens with corresponding antibody molecules, a nucleic acid sequence with its complementary sequence, effector molecules with receptor molecules, enzymes with inhibitors, activators or substrates, sugar chain-containing compounds with lectins, aptamers with its binding partners, an antibody molecule with another antibody molecule specific for the former antibody, receptor molecules with corresponding antibody molecules and the like combinations. Other examples of the specific binding substances include a compound which has been chemically modified to such a degree that its specific binding activity still remains intact and a complex body of a compound bound to other components. Examples of combinations of such types of specific binding substances with the specific substances include: a chemically biotin-modified antibody molecule or polynucleotide with avidin, an avidin-bound antibody molecule with biotin and the like combinations.

The term "binding site" refers to a region or domain of a specific binding substance or active agent which is capable of binding to a target analyte.

The terms "reagent" or "reagents" refer to a substance or a mixture of substances that specifically detects one target analyte. Typically a reagent is a fluorescent labeled binding molecule, antibody, receptor or aptamer. Reagents can be mixed to create a reagent to detect more than one target analyte.

The term "protein" as used herein may be defined as two or more covalently bonded amino acid, which includes proteins, polypeptides, oligopeptides and peptides.

The terms "amino acid" and "peptide", as used herein refer to both naturally occurring and synthetic amino acid and amino acid chains respectively.

The term "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−10 of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

Exemplary, non-limiting embodiments of the invention will now be disclosed.

In one example, it is described a method of encoding a microarray. The method can comprise in a first step depositing at least one batch of particles on a microarray, wherein each batch of particles comprises at least two sub-batches of particles. In case more than one batch of particles is deposited each batch of particles is deposited separately and an image is taken of each batch of particles on the microarray after deposition to identify the position of the particles of each batch on the microarray. In case only one batch of particles is deposited the number of particles of each sub-batch is unique to that sub-batch of particles resulting in a unique particle number ratio for the one batch. In another example, in case at least two batches of particles are deposited the particle number ratio for each batch is either the same or different from each other. Each sub-batch of particles deposited on the microarray is capable of binding to a specific target-analyte, wherein each sub-batch of a batch binds to a different target-analyte compared to all other sub-batches of the respective batch or compared to all other sub-batches of all batches deposited. Furthermore, the method can comprise recording information about the position of particles of the batch(es) and information of the particle number ratio for the batch(es) obtained before for each microarray produced according to this method. The position of the particles and the particle number ratio within a batch allows determining which target analyte is present in a test sample to be analyzed with the microarray or in case only one batch is deposited the particle number ratio of the batch allows determining which target analyte is present in a test sample to be analyzed with the microarray.

In another example, the present invention provides a method of decoding a microarray obtained via a method referred to above. The method can comprise in a first step analyzing an image obtained from an entity which conducted a screening test using a microarray as referred to herein. Analyzing of the image can comprise determining the position and number or intensity of detectable signals obtained from binding of the target analyte to a particle deposited on the microarray. It can further comprise decoding the information obtained above by comparing the information obtained above with the information recorded from the microarray to identify the target analyte bound to the particles of the microarray.

In another example disclosed herein is a method for decoding a bead microarray which does not rely on physical tags or labels and thereby determining the identity of each single microbead in which the bead microarray was formed by a single deposition of a bead batch and in which the bead batch was premixed from at least three sub bead batches and in which the sub bead batches have different bead number ratios to distinguish the sub bead batches from one another and each sub bead batch carries a different binding ligand on its surface to detect a different analyte and in which an optical signal is generated by the sub bead batches in the presents of its respective analyte and the identity of the sub bead batches generating an optical signal is decoded by the bead number ratios of beads generating a optical signal compared to beads not generating an optical signal. As disclosed herein, the identity of single beads can only be decoded by analyzing signals originating from a plurality of beads; in comparison to the state of the art only teaching bead identification by self-encoded beads carrying physical identifier. The decoding information is present in the plurality of beads but not in each single bead.

Advantageously, in another example, there is provided a microarray for detecting the presence of one or more target analytes in a sample, the microarray comprising:

an array of particles having one or more binding sites thereon for binding with said target analytes present in the sample, the particles emitting a change in a detectable signal when a target analyte binds to the binding site of the particle, wherein the particle array comprises at least two particle subsets, each subset having a common binding site to one or more target analytes that are unique to that subset and wherein the number of particles of each subset is known.

The plurality of particles may be present in one or more batches such that each batch of particles may comprise a plurality of sub-batches (or subsets) of particles.

The detectable signal may be an optical signal.

Advantageously, the disclosed method may allow the encoding and decoding of a microarray by a combination of (i) deposition of batches of particles having different particle number ratios based on the particles present in each sub-batch making up that particular batch and (ii) use of a reagent or reagent mixtures that react with known and predetermined target analyte(s) present in the sub-batches or batches of particles.

If more than one batch is deposited, after the deposition of each batch, an image of the microarray may be taken in order to capture the positions of the particles of that batch in the microarray. The image of the current microarray would 'deduct' the image of the previous microarray so that an accurate image of each batch is taken, rather than an image of the cumulative batches. By knowing the positions of the particles making up each batch, the exact batch that reacted with the target analyte may be determined.

The particle ratio based on the number of particles in each sub-batch making up the batch may be predetermined. By knowing the particle ratio, the exact sub-batch that reacted with the target analyte may be determined. For example, the particle ratio of a batch of a microarray (also referred to as particle number ratio) is 5/3/1. Each of the three sub-batches of this batch comprises a different amount of particles or beads according to the ratio 5/3/1, wherein 5 represents sub-batch 1, 3 represents sub-batch 2 and 1 represents sub-batch 3. For example 500 beads, 300 beads and 100 beads, respectively. Now a sample is brought in contact with this microarray which is suspected to comprise target analytes capable of binding to the active agents of the three different sub-batches. The signals measured are equivalent to 400. This would mean that the sample comprised the target analytes which bind specifically to sub-batches 2 and 3 of the batch with the ratio 5/3/1.

Thus, as the reagent used is specific for the target analyte that is bound to the active agent(s), by knowing the exact batch and sub-batch determined from the above, the target analyte can be identified and the microarray can be decoded without the use of physical tags or identifiers linked to the particle(s).

Typically, but not limiting, the active agent bound to the particle may be an antibody (capture antibody), the target analyte is the corresponding antigen and the reagent is a fluorescent labeled antibody (detector antibody), thereby forming a sandwich immune assay. The particle population and its corresponding target analyte is identified by recoding the fluorescence signal and using the disclosed combinatory encoding method. Because the bead batches are identified by combinatory encoding reagents with the same fluorophore for all bead batches, the fluorescence signal from all of the bead batches can be measured using a single wavelength.

If one batch is used, it is not necessary to image the microarray and the microarray can be decoded using the particle ratio of the various sub-batches making up the batch as described exemplarily above.

More advantageously, the disclosed method may allow the encoding and decoding of a microarray without using a physical tag or identifier attached to the particles and by only using a single wavelength in case of optical tests. "Without using a physical tag or identified" means that during the decoding of the information obtained from the microarray the measured optical signal alone is not sufficient to determine which target analytes were present in a test sample. Only the knowledge of the bead ratio (in case of a single batch on the microarray) or the bead ratio and the knowledge of the position of each bead of the different batches (in case more than one batch is comprised on the microarray) allows to identify which target analytes were comprised in the test sample.

Hence, the disclosed method may overcome problems associated with the prior art such as tagging of each individual particle in each batch and use of multi wavelengths readout.

The disclosed method also overcomes interferences between fluorophores and dyes for tagging with fluorophores and dyes for signal generation. As no dyes for tagging are necessary complex optical assays such as FRET assays can be easily incorporated into beads of the present invention.

The ratio of signal intensities was previously used to identify bead batches. However all prior art on signal intensity ratios is based on intensities from optical labels or tags incorporated into the beads. For example, WO2011/127042 teaches the identification of beads by "multimodal distribution patterns" which are defined as "data sets of at least two tagged-beads plotted as bead count versus label intensity" wherein tagged beads refer to "any bead attached to a label i.e. a unique colored bead . . . ". Microbeads employed in WO2011/127042 and US2003/0073086 are self-encoded; the decoding of the beads is possible with information already incorporated into a single bead, typically a color code. In comparison, the signal ratio intensities of the current invention do not originate from pre-incorporated labels or tags. The current invention, in an embodiment, does not rely on physical labels attached to beads and beads are not self-encoded. Instead the decoding information is contained in the plurality of beads and not in each single bead. Only by observing the plurality of beads, typically hundreds to thousands of beads and determining signal intensity ratios of the plurality of beads the bead sub batches can be decoded.

As mentioned above, the microarray may be imaged after deposition of each batch to determine the spatial position of all added particles after each deposition step. The position of all particles for one particular batch "M" is determined by image analysis; wherein the previous image "M−1" is deducted from the current image "M". In this way a data table with positions of all particles of batch "M" is generated. Batch "M" was formed of mixtures of sub batches "m" to "m+x"; wherein "x+1" is the total number of sub-batches of "M". Sub-batches forming batch "M" have different particle number ratios. The identity of sub-batch particles is determined by analysis of particle signals after performing the bioassay, and encoded by the known particle ratio of all batches "m" to "m+x", wherein x is typically but not limited between 1 and 10, that is, 1, 2, 3, 4, 5, 6, 7, 8, 9 or 10. Thereby, a number of up to "x+1" target analytes can be determined in a single deposition batch without having to use a physical tag or identifier to determine which target-analytes bound to the particles. More than one batch can be deposited sequentially and imaged after each deposition. For example, a typical batch may consist of 5 sub-batches to allow the analysis of 5 different target analytes from a single particle deposition step.

The decoding of particles as mentioned above may be combined by sequential reagent incubation to increase the number of particle sub-batches from a single deposition batch which can be encoded. First a batch "M1" is formed of mixtures of sub batches "m1,1" to "m1,1+x1"; wherein "x1+1" is the total number of sub batches of "M1". Then a second batch "M2" is formed of mixtures of sub batches "m2,1" to "m2,1+x2"; wherein "x2+1" is the total number of sub batches of "M2". Further batches "M2" to "Mn" can be formed to create a total number of "n+1" batches; wherein "n" is typically but not limited to 1 to 10, that is, 1, 2, 3, 4, 5, 6, 7, 8, 9 or 10. In all batches "M" to "Mn", the sub-batches for example "m1" to "m1,1+x" are formed by using different particle ratios for each sub-batch. For example, a ratio of 10/5/2/1 for four sub-batches may be used.

Based on this ratio, it can be seen that a batch is formed which contains 10 times more particles of the first sub-batch compared to the last sub-batch, and 5 times more particles of the second sub-batch compared to the last sub-batch and 2 times more particles of the third sub-batch compared to the last sub-batch. Then, batches "M" to "Mn" are mixed together to form a super batch "S1". The super batch is deposited and imaged to determine the spatial location of all beads of the super batch. A set of reagents "R1" to "Rn" corresponding to each batch "M1" to "Mn" is formed wherein for example, reagent "R1" contains all reagents necessary to detect all sub-batches of a batch.

The decoding of beads is performed by sequential reagent application. First, the microarray formed from a single deposition of super batch "S1" is contacted with the sample to cause binding of analytes to its respective active agents on the particles. Then, reagent "R1" is applied and a signal is only generated for beads "m1,1" to "m1,1+x1" if its respective analyte was present in the sample. Because the total number of particles deposited in any given area of the microarray is known and the particle number ratio of sub-batches is known, particles generating a signal can be decoded.

In this way a total of for example 15 analytes can be encoded and detected by sequential incubation of 3 reagents "R1 to R3" each encoding 5 sub-batches of particles with different particle number ratio. It must be noted that only one particle deposition and one imaging step was performed.

Most preferably, particle ratios of prime numbers such as 11/7/5/3/1 are used for more robust batch identification.

Preferably, the known number of particles of each subset is unique to that subset.

A microarray may also be formed from more than one super batch in which super batches "S1" to "Sn" are created. Super batches "S1" to "Sn" are sequentially deposited and imaged after each deposition step to determine the position of all particles of the respective super batch.

After sample incubation, particles are decoded by sequential incubation with reagents "R1 to "Rn"; wherein "R1" contains all reagents to encode all particles of the first batch "M1" in each super batch; "R2" contains all reagents to encode all particles of the second batch "M2" in each super batches and so on. The total numbers of beads "T" which can be encoded by this method is: T=Number of batches× number of sub-batches×number of super-batches.

It is also to be noted that other microarrays having different numbers of sub-batches, batches and super-batches as well as different particle ratios may be formed and are not limited to those specific examples above.

The number of possible target analytes to be encoded may be further increased by using the same sub-batch in two or more different batches and those batches are sequentially deposited to determine the spatial positions of all particles in the batch. This advanced combination encoding method can be best disclosed with a non limiting example. For example, 6 batches "M1" to "M6" are prepared. Each batch consists of multiple sub-batches "SB1" to "SBx". Batches are now formed in the following way; different combinations of sub-batches in batches are created, for example, sub-batch SB1 is present only in batch M1; sub-batch SB2 is present in batch M1 and M2; sub-batch SB3 is present in batch M1, M2 and M3; sub-batch SB4 is present in batch M4; sub-batch SB5 is present in batch M2 and M3; sub-batch SB6 is present in batches M2, M3 and M4; sub-batch SB7 is present in batches M4 and M5; sub-batch SB8 is present in all batches; and so forth. Hence, batch M1 contains SB1, SB2, Sb3 and SB8; batch M2 contains SB2, SB3, SB5, SB6 and SB8; batch M3 contains SB3, SB5, SB6 and SB8; batch M4 contains SB4, SB6, SB7 and SB8; batch M5 contains SB7 and SB8; and batch M6 contains SB8 only. The highest encoding number is reached when every combination of the sub-batches in the batches is reached. The sub-batch combinations are all known and spatial positions of all particles of a batch are known. By using a single sample and reagent incubation, all particles can be decoded. For example, if a signal is generated only in batches M1, M2 and M3, the corresponding analyte to particles of sub-batch SB3 is present.

This method can be further combined using different particle number ratios to better distinguish sub-batches from one another. With this powerful combination encoding method, a very large number of different sub-batches, each detecting a different analyte, can be encoded and microarrays with high multiplex capabilities can be produced with lesser number of particle deposition steps.

A preferred embodiment of the current invention is using the Landau function in combination with prime number bead ratios, wherein the objective is to maximize the number of bead sub-batches for a given number of bead batches, in order to reduce the number of particle deposition steps required. For a given number of bead sub-batches 'n', the batches are partitioned in such a way that no bead sub-batch appears more than once in the subgroup of bead batch. The best possible partition of the bead batches with every sub-batch occurring only once in the subgroup of bead batches is represented by the Landau's function g(n). It is defined for every natural number n to be the largest order of an element of the symmetric group $S_n$. Equivalently, g(n) is the largest least common multiple (LCM) of any partition of n, or the maximum number of times a permutation of n elements can be recursively applied to itself before it returns to its starting sequence.

For instance, 5=2+3 and LCM (2, 3)=6. No other partition of 5 yields a bigger LCM, so g(5)=6. An element of order 6 in the group $S_5$ can be written in cycle notation as (1 2) (3 4 5).

If "s" combinations of ratios can be found such that each ratio is unique and the sum of proportions is also unique for all possible combinations. Then by depositing the bead sub-batches using the ratios c*s bead sub-batches can be encoded using the same number of bead batches. For e.g. for n=13 if the first bead sub-batch is encoded in bead batches 1 and 7 then we expect the 43rd bead sub-batch also to be encoded into the bead batches 1 and 7 (see table 1 below). In such a way if the beads of batch 1 are encoded in bead pools with a particular ratio while the beads of batch 43 are encoded into the same two pools in a different ratio, decoding can still be achieved based on the ratios. Advantageously, ratios of prime numbers are used such that the sum of the proportions is never equal to the another proportion value, e.g. 1:2:3:5 2+3 adds up to 5 so such combinations should be avoided and instead can follow a ratio as follows 1:3:5:7:11 and so on.

Decoding by Pooling

LCM=6*7=42 (Since we divide 13 groups in subgroups of 6 and 7)

TABLE 1

Example of how to maximize number of bead sub-batches encoded by a fixed number of batches.

| Bead batch No. | Bead Pool No. 1 | 2 | 3 | 4 | 5 | 6 | 7 | 8 | 9 | 10 | 11 | 12 | 13 |
|---|---|---|---|---|---|---|---|---|---|---|---|---|---|
| 1 | 1 | | | | | | 1 | | | | | | |
| 2 | | 1 | | | | | | 1 | | | | | |
| 3 | | | 1 | | | | | | 1 | | | | |
| 4 | | | | 1 | | | | | | 1 | | | |
| 5 | | | | | 1 | | | | | | 1 | | |
| 6 | | | | | | 1 | | | | | | 1 | |
| 7 | 1 | | | | | | | | | | | | 1 |
| 8 | | 1 | | | | | 1 | | | | | | |
| 9 | | | 1 | | | | | 1 | | | | | |
| 10 | | | | 1 | | | | | 1 | | | | |
| 11 | | | | | 1 | | | | | 1 | | | |
| 12 | | | | | | 1 | | | | | 1 | | |
| 13 | 1 | | | | | | | | | | | 1 | |
| 14 | | 1 | | | | | | | | | | | 1 |
| 15 | | | 1 | | | | 1 | | | | | | |
| 16 | | | | 1 | | | | 1 | | | | | |
| 17 | | | | | 1 | | | | 1 | | | | |
| 18 | | | | | | 1 | | | | 1 | | | |
| 19 | 1 | | | | | | | | | | 1 | | |
| 20 | | 1 | | | | | | | | | | 1 | |
| 21 | | | 1 | | | | 1 | | | | | | 1 |
| 22 | | | | 1 | | | | 1 | | | | | |
| 23 | | | | | 1 | | | | 1 | | | | |
| 24 | | | | | | 1 | | | 1 | | | | |
| 25 | 1 | | | | | | | | | 1 | | | |
| 26 | | 1 | | | | | | | | | 1 | | |
| 27 | | | 1 | | | | | | | | | 1 | |
| 28 | | | | 1 | | | | | | | | | 1 |
| 29 | | | | | 1 | | 1 | | | | | | |
| 30 | | | | | | 1 | | 1 | | | | | |
| 31 | 1 | | | | | | | | 1 | | | | |
| 32 | | 1 | | | | | | | | 1 | | | |
| 33 | | | 1 | | | | | | | | 1 | | |
| 34 | | | | 1 | | | | | | | | 1 | |
| 35 | | | | | 1 | | | | | | | | 1 |
| 36 | | | | | | 1 | 1 | | | | | | |

TABLE 1-continued

Example of how to maximize number of bead sub-batches encoded by a fixed number of batches.

| | | | | | | | | | | | | | | |
|---|---|---|---|---|---|---|---|---|---|---|---|---|---|---|
| 37 | 1 | | | | | | | 1 | | | | | | |
| 38 | | 1 | | | | | | | 1 | | | | | |
| 39 | | | 1 | | | | | | | 1 | | | | |
| 40 | | | | 1 | | | | | | | 1 | | | |
| 41 | | | | | 1 | | | | | | | 1 | | |
| | | | | | | 1 | | | | | | | | LCM = |
| 42 | | | | | | | | | | | | | 1 | 42 |
| 43 | 2 | | | | | | 1 | | | | | | | |
| 44 | | 2 | | | | | | 1 | | | | | | |
| 45 | | | 2 | | | | | | 1 | | | | | |
| 46 | | | | 2 | | | | | | 1 | | | | |
| 47 | | | | | 2 | | | | | | 1 | | | |
| 48 | | | | | | 2 | | | | | | 1 | | |
| 49 | 2 | | | | | | | | | | | | 1 | |
| 50 | | 2 | | | | | 1 | | | | | | | |
| 51 | | | 2 | | | | | 1 | | | | | | |
| 52 | | | | 2 | | | | | 1 | | | | | |
| 53 | | | | | 2 | | | | | 1 | | | | |
| 54 | | | | | | 2 | | | | | 1 | | | |
| 55 | 2 | | | | | | | | | | | 1 | | |
| 56 | | 2 | | | | | | | | | | | 1 | |
| 57 | | | 2 | | | | 1 | | | | | | | |
| 58 | | | | 2 | | | | 1 | | | | | | |
| 59 | | | | | 2 | | | | 1 | | | | | |
| 60 | | | | | | 2 | | | | 1 | | | | |
| 61 | 2 | | | | | | | | | | 1 | | | |
| 62 | | 2 | | | | | | | | | | 1 | | |
| 63 | | | 2 | | | | | | | | | | 1 | |
| 64 | | | | 2 | | | 1 | | | | | | | |
| 65 | | | | | 2 | | | 1 | | | | | | |
| 66 | | | | | | 2 | | | 1 | | | | | |
| 67 | 2 | | | | | | | | | 1 | | | | |
| 68 | | 2 | | | | | | | | | 1 | | | |
| 69 | | | 2 | | | | | | | | | 1 | | |
| 70 | | | | 2 | | | | | | | | | 1 | |
| 71 | | | | | 2 | | 1 | | | | | | | |
| 72 | | | | | | 2 | | 1 | | | | | | |
| 73 | 2 | | | | | | | | 1 | | | | | |
| 74 | | 2 | | | | | | | | 1 | | | | |
| 75 | | | 2 | | | | | | | | 1 | | | |
| 76 | | | | 2 | | | | | | | | 1 | | |
| 77 | | | | | 2 | | | | | | | | 1 | |
| 78 | | | | | | 2 | 1 | | | | | | | |
| 79 | 2 | | | | | | | 1 | | | | | | |
| 80 | | 2 | | | | | | | 1 | | | | | |
| 81 | | | 2 | | | | | | | 1 | | | | |

TABLE 1-continued

| Example of how to maximize number of bead sub-batches encoded by a fixed number of batches. | | | | | | | | | | | | | | |
|---|---|---|---|---|---|---|---|---|---|---|---|---|---|---|
| 82 | | | | 2 | | | | | | | 1 | | | |
| 83 | | | | | 2 | | | | | | | 1 | | |
| 84 | | | | | | 2 | | | | | | | 1 | |
| 85 | 1 | | | | | | 3 | | | | | | | |
| 86 | | 1 | | | | | | 3 | | | | | | |
| 87 | | | 1 | | | | | | 3 | | | | | 42 + 42 |
| 88 | | | | 1 | | | | | | 3 | | | | |
| 89 | | | | | 1 | | | | | | 3 | | | |
| 90 | | | | | | 1 | | | | | | 3 | | |
| 91 | 1 | | | | | | | | | | | | 3 | |
| 92 | | 1 | | | | | 3 | | | | | | | |
| 93 | | | 1 | | | | | 3 | | | | | | |
| 94 | | | | 1 | | | | | 3 | | | | | |
| 95 | | | | | 1 | | | | | 3 | | | | |
| 96 | | | | | | 1 | | | | | 3 | | | |
| 97 | 1 | | | | | | | | | | | 3 | | |
| 98 | | 1 | | | | | | | | | | | 3 | |
| 99 | | | 1 | | | | 3 | | | | | | | |
| 100 | | | | 1 | | | | 3 | | | | | | |
| 101 | | | | | 1 | | | | 3 | | | | | |
| 102 | | | | | | 1 | | | | 3 | | | | |
| 103 | 1 | | | | | | | | | | 3 | | | |
| 104 | | 1 | | | | | | | | | | 3 | | |
| 105 | | | 1 | | | | | | | | | | 3 | |
| 106 | | | | 1 | | | 3 | | | | | | | |
| 107 | | | | | 1 | | | 3 | | | | | | |
| 108 | | | | | | 1 | | | 3 | | | | | |
| 109 | 1 | | | | | | | | | 3 | | | | |
| 110 | | 1 | | | | | | | | | 3 | | | |
| 111 | | | 1 | | | | | | | | | 3 | | |
| 112 | | | | 1 | | | | | | | | | 3 | |
| 113 | | | | | 1 | | 3 | | | | | | | |
| 114 | | | | | | 1 | | 3 | | | | | | |
| 115 | 1 | | | | | | | | 3 | | | | | |
| 116 | | 1 | | | | | | | | 3 | | | | |
| 117 | | | 1 | | | | | | | | 3 | | | |
| 118 | | | | 1 | | | | | | | | 3 | | |
| 119 | | | | | 1 | | | | | | | | 3 | |
| 120 | | | | | | 1 | 3 | | | | | | | |
| 121 | 1 | | | | | | | 3 | | | | | | |
| 122 | | 1 | | | | | | | 3 | | | | | |
| 123 | | | 1 | | | | | | | 3 | | | | |
| 124 | | | | 1 | | | | | | | 3 | | | |
| 125 | | | | | 1 | | | | | | | 3 | | |
| 126 | | | | | | 1 | | | | | | | 3 | |

The number of bead sub-batches that can uniquely be encoded can further be increased by depositing each bead sub-batch in more than just a pair of bead batches. For e.g. for n=20, depositing each bead sub-batch in 3 bead batches, one possible value can be c=LCM(5, 7, 8)=280. In general, for n bead batches and if each bead sub-batch is deposited in k bead batches then the number of unique encodings is c=LCM(m1.m2.M3 . . . mk) such that m1+m2+m3+ . . . +mk=n.

It should be noted that the disclosed method does not use any physical tag or identifier and only relies on combination encoding/decoding. The permutations of sub-batches in batches provide a decoding key for microarrays of the disclosed method and only the holder of the decoding key can make use of the analytical information.

The above combination methods are further illustrated in Examples 1 to 6 below. It is to be noted that different combination methods can be combined to achieve a higher encoding. The numbers given in these examples are only for illustration purpose and do not represent limitations of the methods.

The particle may be a bead or a biological entity such as a cell, a bacteria or a virus particle. In embodiments where the particle is a microbead, the microbead may be an irregularly shaped microbead or a regularly shaped microbead. The microbead may also have a shape selected from the group consisting of microsphere, microcapsule, microrod, microcube and microtube. In one embodiment, the microbead is a microsphere.

The microbead may be formed of a material selected from plastic, ceramic, glass, metal, a metal oxide, silicon dioxide, polystyrene, methylstyrene, acrylic polymer, sepharose, cellulose, nylon, cross-linked micelles, Teflon, paramagnetic-material, thoria sol, carbon graphite, titanium dioxide, latex or cross-linked dextran such as sepharose, cellulose, nylon, cross-linked micelle and teflon or with similar compositions used in peptide, nucleic acid and organic moiety synthesis or mixtures thereof, for example, metal filled polymer particles.

Methods of how to bind particles to the surface of a microarray are known in the art. In the present invention the particles are considered to be attachable to the surface of the microarray, for example via a linker. It is also possible to localize particles on the substrate of a microarray by providing a grit comprising wells. Each well is capable of holding exactly one particle. This method can be used in combination with a method where for example the particles comprise a linker for attachment to the surface of the microarray.

In embodiments where the particle is a cell, the cell may be a living cell or a dead cell. The cell particles may be applied as a cell suspension containing single cells or as a cluster of cells and deposited by any methods described above to produce cell microarrays.

If a large surface area is desired, the particle may be at least partially porous. For porous particles, reactions to perform a physical, chemical, biochemical, enzymatic or immunoassay may be carried out both on the surface of the particle and in the interior of the particle. Porous particles may have diffusion properties controlled by their porosity and permeability to exclude unwanted or interfering molecules from diffusion into the interior. Porous particles may also have diffusion properties to entrap active agents such as enzymes, antibodies, DNA, cells or reagents from diffusing out and thereby entrapping or immobilizing them into the interior. Accordingly, the particle may be at least partially porous or has a porous capsule to allow the passage of desired analytes into the interior of the particle.

The particle may have a particle size in the range from about 0.1 micron to about 500 microns, or from about 1 micron to about 10 microns. Each particle may comprise at least one active agent that is attached to, or incorporated within, the particle structure that is capable of specific binding with at least one target analyte. In one embodiment, the particle comprises a single type of active agent. In another embodiment, the particle may comprise at least two active agents, each agent may independently from each other be a chemical agent or a bioactive agent. The at least two active agents can be provided with a known binding site number ratio.

The active agent that may be attached to the particles may be an organic compound or an inorganic compound. The organic active agent may include, but is not limited to peptides, proteins, nucleic acids, metabolites, carbohydrates, enzymes, antibodies, hormones, lectines, drugs, pesticides, allergens, antigens, receptors, fatty acids or mixtures thereof.

The protein may be a naturally occurring protein or a synthetically synthesized protein. The protein may be obtained from cellular extracts or from random or directed digests of proteinaceous cellular extracts.

The nucleic acid may be naturally occurring or synthetically synthesized. The nucleic acid may be single stranded or double stranded or contain portions of both double stranded or single stranded sequence. The nucleic acid may be DNA, both genomic and cDNA, RNA or a hybrid.

The active agents may be modified through conventional chemical, physical and biochemical means prior to attachment on the particles.

The active agents may either be synthesized directly on the particles, or they may be made and then attached after synthesis. In one embodiment, linkers are employed to attach the active agents to the particles, to provide better attachment, improve interaction with the target molecule due to the increased flexibility, and to reduce undesirable or non-specific binding. The attachment of the active agent onto the particle may be dependent on chemical interactions selected from the group consisting of electrostatic interaction, ionic bonds, covalent bonds, hydrogen bonds and dipole-dipole interaction. Prior to attaching of the active agent to the particle, the particle may be functionalized with chemically reactive groups to facilitate binding.

The particles may be placed on a substrate support. The substrate material may be selected from synthetic or naturally occurring polymeric materials, organic materials, inorganic materials, metals, ceramics, plastic, rubber, glass, fibrous materials, graphite or silicon. Exemplary substrates are selected from the group consisting of silicon, silicon dioxide, silicon nitride, modified silicon, glass and modified or functionalized glass, inorganic glasses, plastics, acrylics, polystyrene and copolymers of styrene, polypropylene, polyethylene, polybutylene, polyurethanes, Teflon, polysaccharides, nylon, nitrocellulose, resins, silica, silica-based materials, carbon and metals. In one embodiment, the substrate does not auto-fluoresce.

The target analyte may be organic or inorganic molecules. The target analyte may be selected from the group consisting of environmental pollutants (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, enzyme, antibodies, antigens, cellular membrane antigens and receptors (neural, hormonal, nutrient, and cell surface receptors) or their ligands, etc); whole cells (including prokaryotic (such as pathogenic bacteria) and eukaryotic cells, including mammalian tumor cells); viruses (including retroviruses, herpesviruses, adenoviruses, lentiviruses, etc.); and spores. The target analytes may be nucleic acids and proteins (including immunoglobulins; enzymes, hormones and cytokines). The specific binding of the target analyte to the bioactive agent may be dependent on chemical interactions selected from the group consisting of electrostatic interaction, ionic bonds, covalent bonds, hydrogen bonds and dipole-dipole interactions.

The reagent may be a substance that specifically detects one target analyte. The reagent may be a mixture of substances, each substance in the mixture detecting one specific target analyte. The reagent may be a fluorescent labeled binding molecule, an antibody, a receptor or an aptamer.

When the microarray is being used to analyse a sample potentially containing a target analyte, the particles may be tagged with an identifier including, but not limited to a fluorescent tag, a bar code, a chemical identifier, a quantum dot, a microstructure, a nucleic acid identifier, an engraving and a radio frequency tag. The identifier may also be added to the target analyte.

Advantageously, the identifier may be used to enhance the identification of the location of the particles and subsequently the active agents on the particles.

When the microarray is used to analyse a sample potentially containing a target analyte, one or more target analytes may be exchanged against a calibrator. The calibrator is a reagent that binds to its corresponding active agent and provides a known optical signal strength. Advantageously, this signal strength can be used for normalization to determine the quantitative concentrations of analytes in a sample.

The identifier may exhibit a change when the active agent binds to the target analyte. This change may be viewed optically under an imaging apparatus or colorimetric apparatus. In one embodiment, the identifier may be applied after the sample containing the target analytes have bound to the active agents of the particles.

The identifier may be conjugated on the target analyte which in turn binds to the corresponding active agent on the particle. The identifier may be directly conjugated to the target analyte or indirectly conjugated to the target analyte by means of a linker molecule or a detector antibody or a secondary antibody.

In an embodiment where the identifier is a fluorescent tag, the fluorescent tag may be a mixture of reporter dyes. The variation of the composition of the mixture of reporter dyes may change the output optical signal intensity, providing a large possible range of unique optical signatures.

The optical signature may be detected with a detector, such as an optical detector. The optical detector may send a signal to the computer memory which is then accessed by a computer processor for generating an image file. Data associated with the image file such as the position and type of particle which exhibits the optical signature is then compared with the data obtained after each particle batch deposition, i.e. the encoding/decoding data table, to identify the identity or the batch of the particle. Those particles which exhibit the optical signature are those which have bound with the target analyte. As the active agent for the subpopulation of the particles is known from the encoding/decoding data table, it is possible to identify the target analytes in the sample.

The disclosed method may enable particle arrays with high multiplexing capabilities to be produced. Advantageously, multiplex microarrays can be produced with a single particle deposition step with particles that do not carry a physical identifier or tag.

The particle array made according to the disclosed process may be used for analytical purposes. Here, a sample is brought into contact with the particle array.

When the sample contains a target analyte that binds to the active agent on the particles, a signal would be generated as a result of this binding. For example, the active agent may be an antibody and the target analyte may be an antigen that binds to the antibody active agent. The antigen may be tagged with a fluorescent tag such that a fluorescent signal is generated upon antibody-antigen binding. The analyte may be directly labeled by a chemical reaction with the fluorophore or by using a second fluorescent labeled detector antibody.

Assays for different analytes may have different accuracy, precision and robustness. This fact arises from intrinsic differences in the antibodies or other binding molecules, such as different antibody quality, binding constants, binding kinetics and impurities. In practice, the assay with less robustness and/or precision would be chosen for the largest particle number and the most robust assay would be chosen for the smallest particle number.

The disclosed method may provide an alternative method to fabricate particle microarray device for analysis and quantification of biological, chemical or physical parameters.

Further, there is provided a microarray system for identifying the presence of one or more target analytes in a sample comprising: a micro-array comprising a substrate having a plurality of chemically or biologically active particles that are lockingly engaged with the substrate; a memory recording the location of each particle, said location of each particle having been determined by imaging of the substrate; a detector to detect changes in the particles upon contact with the sample; and a processor responsive to program instructions to interrogate the memory and to compare data received from the detector to identify the presence of the one or more target analytes in the sample based on the location of each particle.

The image of the location of the particle may be recorded in the encoding/decoding data table in the memory of a computer. The image can therefore be readily accessed by the processor acting under instructions of a computer program to decode the microarray by determining the position of the particle and the particle number ratio of the batch and the applied reagent.

In another embodiment of the present invention, the particle number ratio concept is applied to the binding sites of different analytes on the same particle batch.

For example, for 3 target analytes A1, A2, and A3, two particle batches B1 and B2 are prepared and the number of binding sites present on the particles is known. This number is then used to generate a known binding site number ratio. For example, the B1 particle batch may carry the binding sites for target analytes A1 and A2 in a binding site number ratio of 11/3 respectively, whereas the B2 particle batch may carry the binding sites for target analytes A2 and A3 in a binding site number ratio of 11/3 respectively.

In the above example, a detected signal intensity ratio of 3/11 for particle batches B1/B2 would indicate that only target analyte A2 is present in the sample. Conversely, if a signal is detected only in particle batch B1, this would indicate that only analyte A1 is present in the sample, whilst a detected signal only in particle batch B2 would indicate that only analyte A3 is present in the sample. The above method provides an additional way to reduce the number of bead batches. Advantageously, both number ratio methods may be combined to provide a multi dimensional encoding method.

Computer Network

Figure 3:
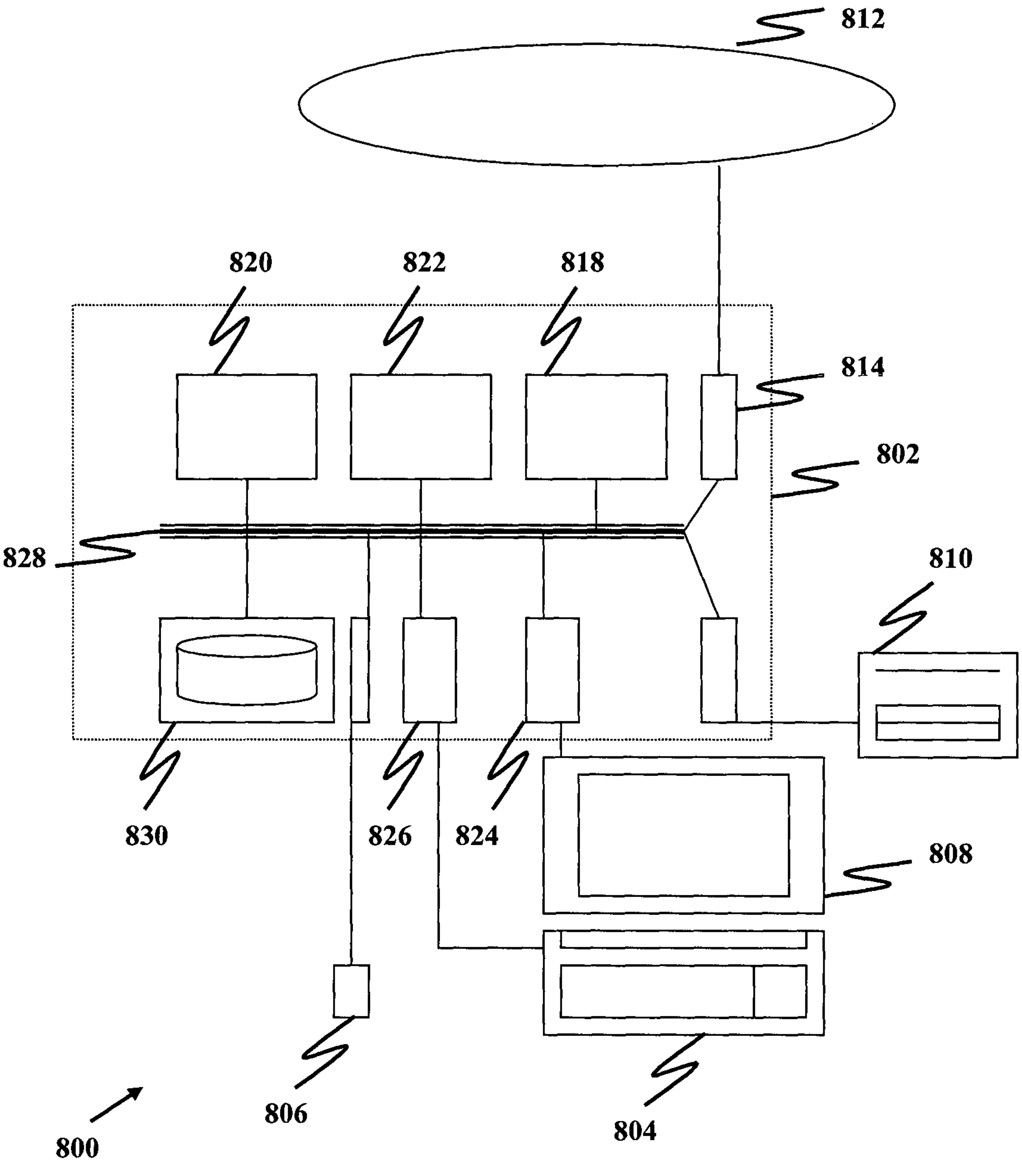
FIG. 3 is a schematic diagram showing the components of a computer system according to an embodiment of the present invention.

The method and system of an embodiment of the invention may be implemented using a computer system 800, schematically shown in FIG. 3. At least part of the embodiment may be implemented as software, such as a computer program being executed within the computer system 800, and instructing the computer system 800 to conduct the method of the example embodiment.

The computer system 800 may comprise a computer module 802, input modules such as a keyboard 804 and mouse 806 and a plurality of output devices such as a display 808, and printer 810.

The computer module 802 may be connected to a computer network 812 via a suitable transceiver device 814, to enable access to e.g. the Internet or other network systems such as Local Area Network (LAN) or Wide Area Network (WAN).

The computer module 802 in the example may include a processor 818, a Random Access Memory (RAM) 820 and a Read Only Memory (ROM) 822. The computer module 802 may also include a number of Input/Output (I/O) interfaces, for example I/O interface 824 to the display 808, and I/O interface 826 to the keyboard 804.

The components of the computer module 802 may typically communicate via an interconnected bus 828 and in a manner known to the person skilled in the relevant art.

The application program may typically be supplied to the user of the computer system 800 encoded on a data storage medium such as a CD-ROM or flash memory carrier and read utilising a corresponding data storage medium drive of a data storage device 830. The application program may be read and controlled in its execution by the processor 818. Intermediate storage of program data maybe accomplished using RAM 820.

FIG. 1 is a schematic diagram showing the components of a system according to an embodiment of the present invention, which include a microarray 100 according to an embodiment of the present invention, a detector 102 for detecting the change in detectable signal emitted by the particles of the microarray and a processor 104 for counting the number of particles emitting a change in the detectable signal.

Figure 2:
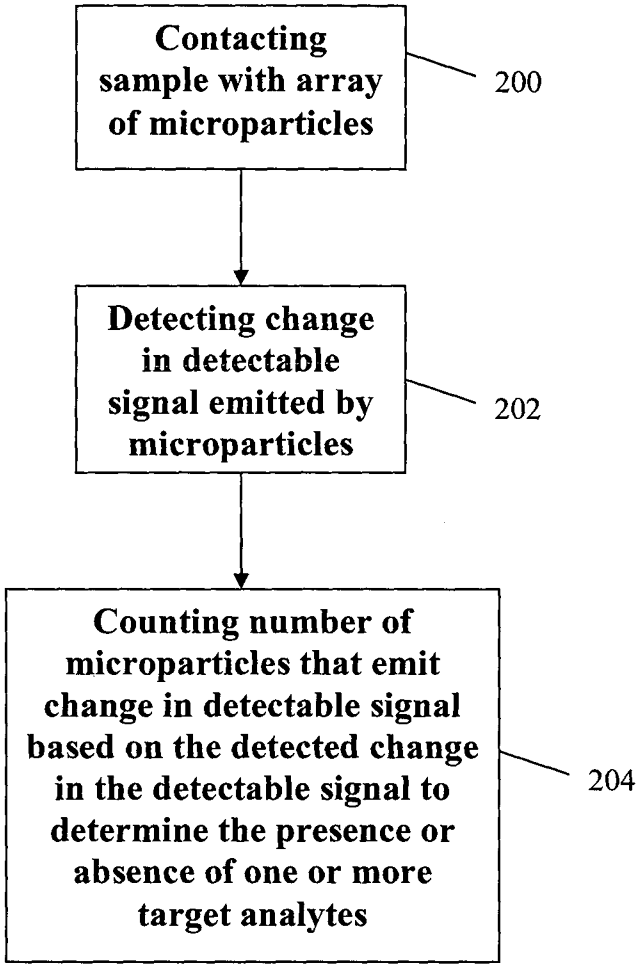
FIG. 2 is a flow chart showing the steps involved in a method according to an embodiment of the present invention for determining the presence of one or more target analytes in a sample.

FIG. 2 is a flow chart showing the steps involved in a method according to an embodiment of the present invention for determining the presence of one or more target analytes in a sample, comprising:

contacting the sample with an array of particles having one or more binding sites thereon for binding with said target analytes present in the sample, the particles emitting a change in a detectable signal when a target analyte binds to at least one of the binding sites of a particle, wherein the particle array comprises at least two particle subsets, each subset having at least one binding site to one or more target analytes that are unique to that subset and wherein the number of particles of each subset is known (step 200);

detecting the change in the detectable signal emitted by the particles (step 202); and counting the number of particles that emit a change in a detectable signal based on the detected change in the detectable signal to determine the presence or absence of one or more target analytes that are unique to said particle subsets (step 204).

FIG. 3 is a schematic diagram showing components of a computer system according to an embodiment of the present invention.

In this non-limiting example, the computer system 800 comprises a computer module 802, input modules such as a keyboard 804 and mouse 806 and a plurality of output devices such as a display 808, and printer 810.

The computer module 802 is connected to a computer network 812 via a suitable transceiver device 814, to enable access to e.g. the Internet or other network systems such as Local Area Network (LAN) or Wide Area Network (WAN).

The computer module 802 includes a processor 818, a Random Access Memory (RAM) 820 and a Read Only Memory (ROM) 822. The computer module 802 also includes a number of Input/Output (I/O) interfaces, for example I/O interface 824 to the display 808, and I/O interface 826 to the keyboard 804.

The components of the computer module 802 communicate via an interconnected bus 828 and in a manner known to the person skilled in the relevant art.

The application program is supplied to the user of the computer system 800 encoded on a data storage medium such as a CD-ROM or flash memory carrier and read utilising a corresponding data storage medium drive of a data storage device 830. The application program is read and controlled in its execution by the processor 818. Intermediate storage of program data is accomplished using RAM 820.

FIGS. 4A to 4F are images of exemplary microarrays of the present invention when used to detect the presence of one or more target analytes in a sample. The upper panels are light microscopy images whilst the lower panels are fluorescent (FITC) microscopy images.

Figure 4A:
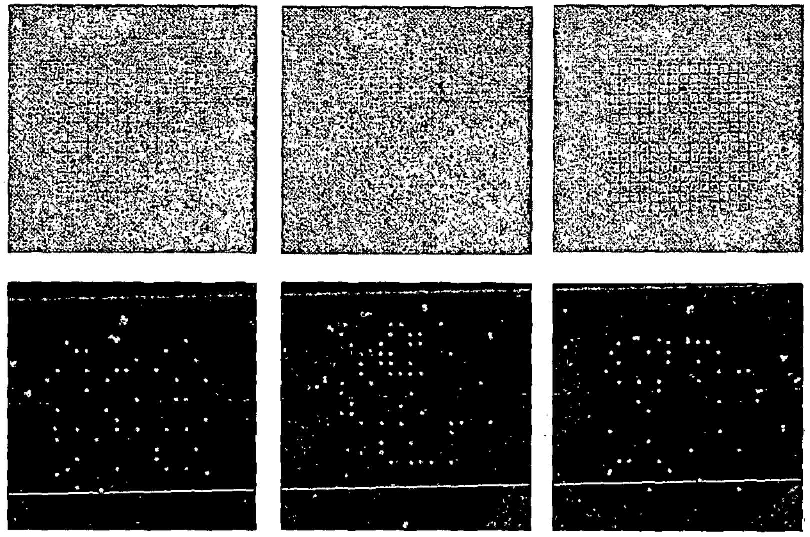
FIGS. 4A to 4F are images of exemplary microarrays of the present invention. The upper panels are light microscopy images whilst the lower panels are fluorescent microscopy images.

FIG. 4A is an image of a microarray which has been incubated with a sample which only contains target analyte A.

Figure 4B:
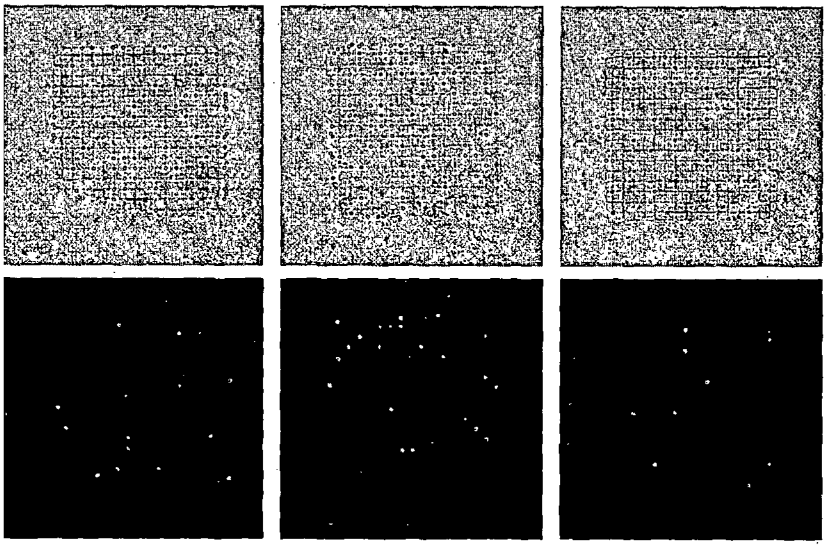

FIG. 4B is an image of a microarray which has been incubated with a sample which only contains target analyte B.

Figure 4C:
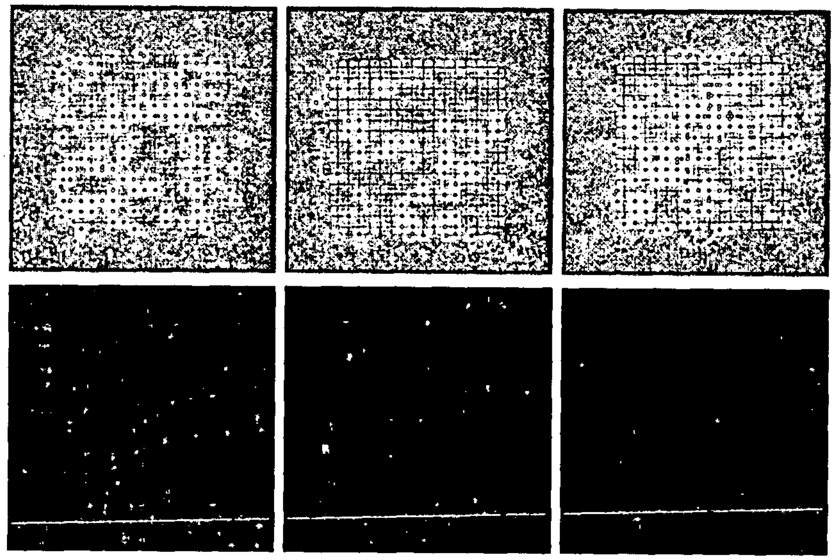

FIG. 4C is an image of a microarray which has been incubated with a sample which only contains target analyte C.

Figure 4D:
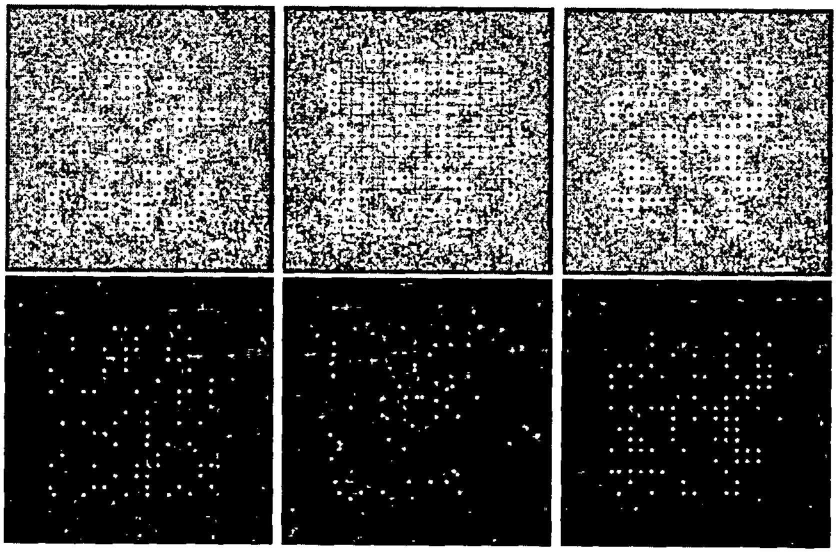

FIG. 4D is an image of a microarray which has been incubated with a sample which contains target analytes A and B.

Figure 4E:
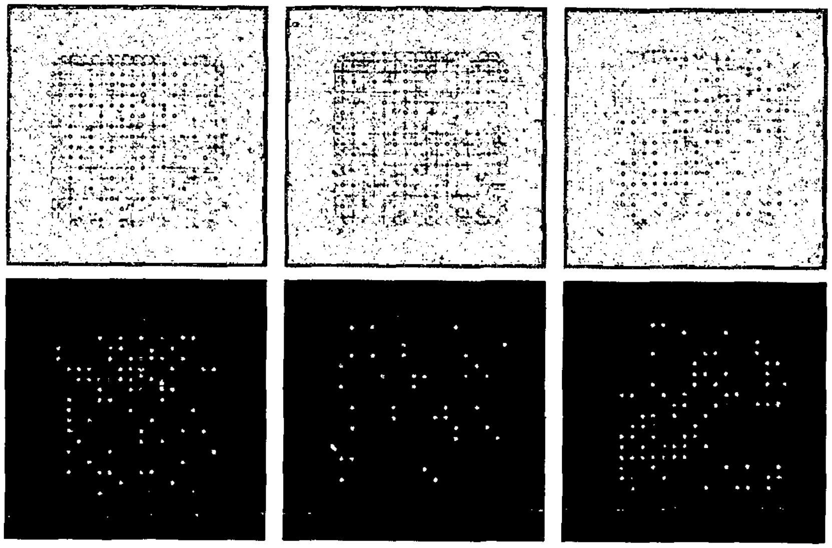

FIG. 4E is an image of a microarray which has been incubated with a sample which contains target analytes A and C.

Figure 4F:
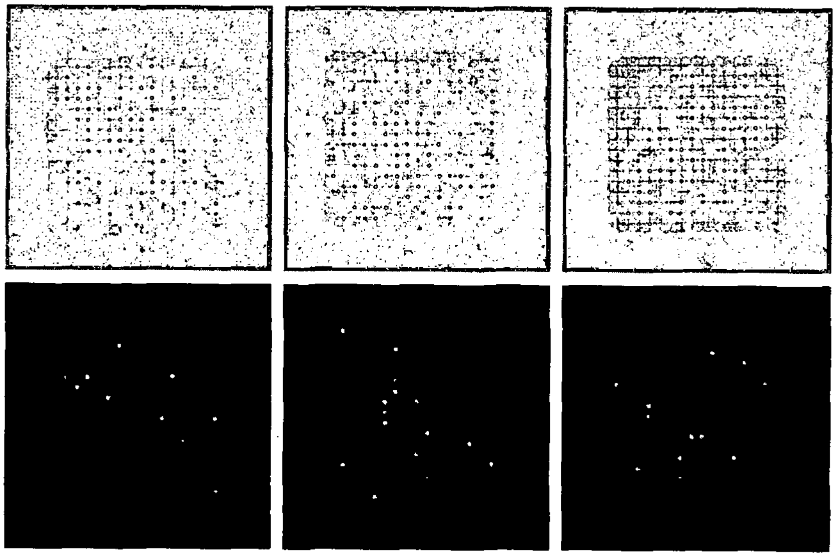

FIG. 4F is an image of a microarray which has been incubated with a sample which contains target analytes B and C.

Figure 5:
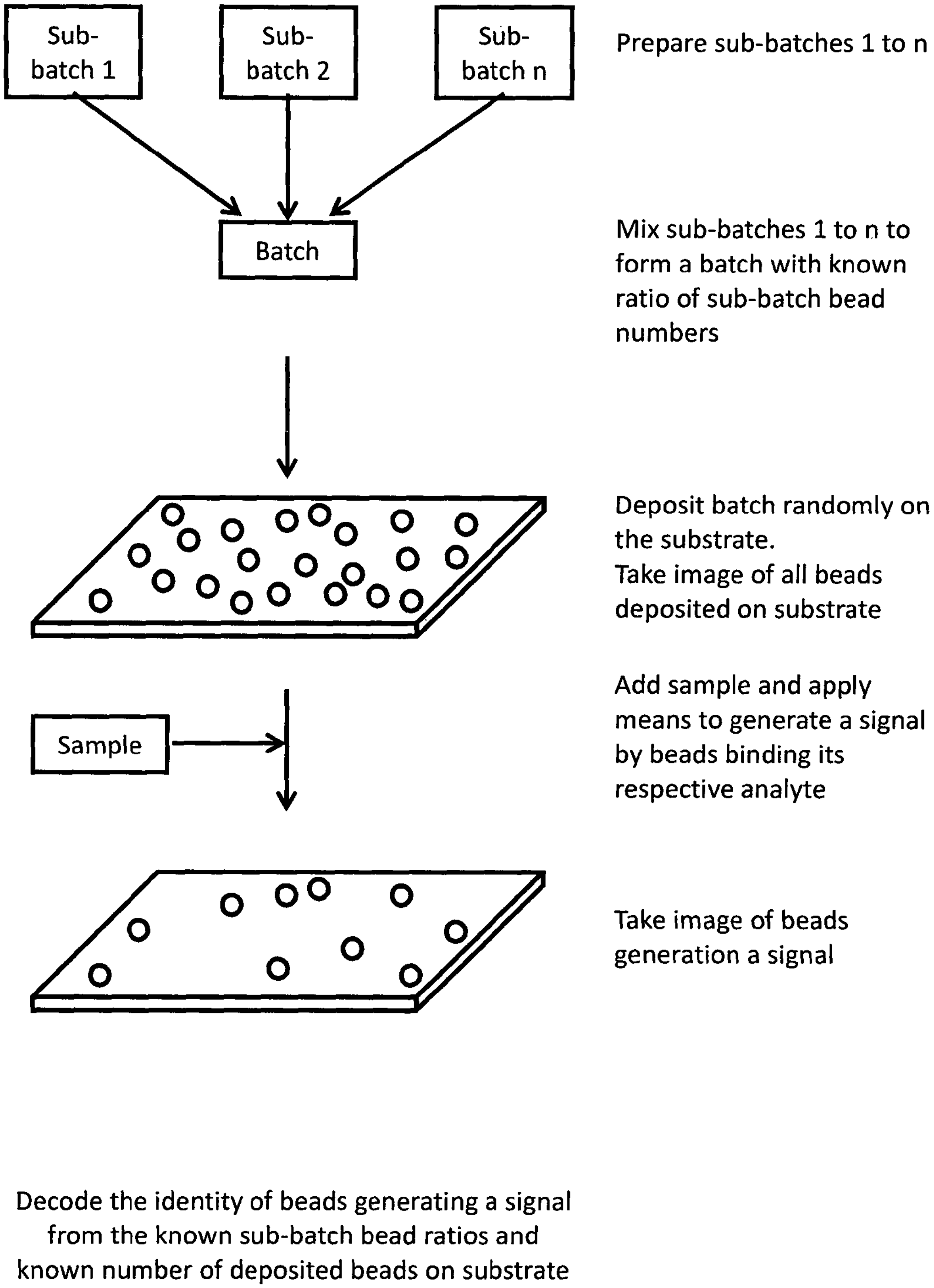
FIGS. 5 and 6 provide images illustrating the encoding and decoding method of the present invention.

FIG. 5 shows an example of the encoding method of the present invention as well as the following decoding method. In this example only one batch comprising three sub-batches is used. However, it is possible to use more than three sub-batches (1 to n). After the sub-batches have been mixed together they are deposited and bound on the surface of material that is to become the microarray. The particles of the sub-batches are mixed together in different amounts to result in a specific particle number ratio. For example, sub-batch 1 comprises 1000 particles, sub-batch 2 comprises 400 particles and sub-batch 3 comprises 100 particles resulting in a bead ratio of 10/4/1. After deposition, the microarray is contacted with a test sample which is suspected to comprise one or more target analytes which can specifically bind to a respective sub-batch. After contacting and incubating the microarray with the test sample for a time sufficient to allow binding of the target analytes to the particles an image is taken to determine which particle generates a signal due to binding to its target analyte.

In case 1000 signals are measured it can be concluded that the target analyte binding to sub-batch 1 was comprised in the test sample. In case 100 signals are measured only the target analyte binding to the third sub-batch was comprised in the test sample. In case all particles generate a signal it is clear that all 3 target analytes were present in the test sample.

It is noted that in this example in which only one batch is used the imaging step is not necessary to later decode which target analyte was comprised in a test sample. In this example, the particle number ratio alone is sufficient to determine whether target analyte specific for sub-batch 1, 2 or 3 was present in the test sample.

Figure 6:
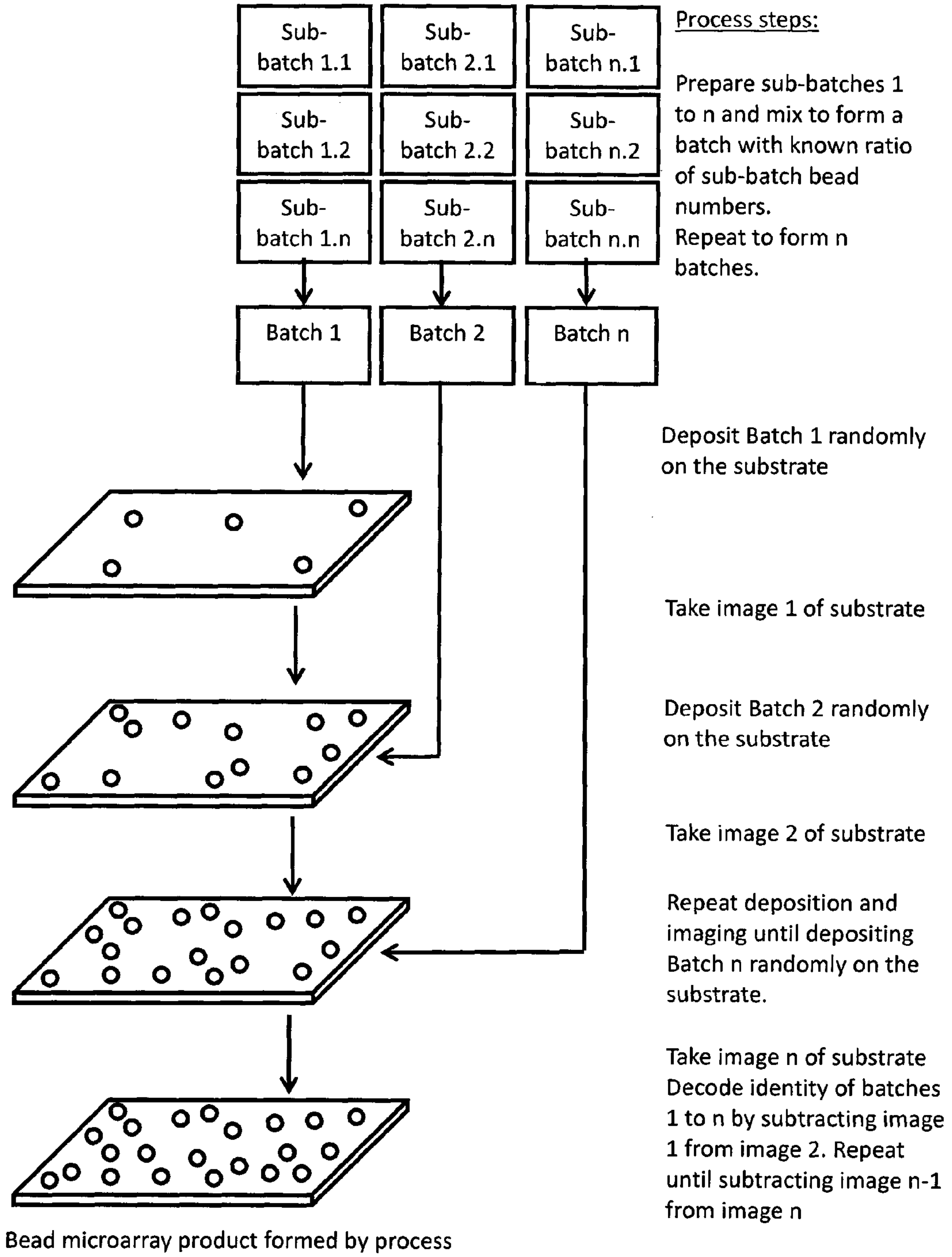

FIG. 6 also shows an encoding and decoding method of the present invention. Compared to the example shown in FIG. 5, the example shown in FIG. 1 uses not only one batch but several batches. To assign a signal to a specific target analyte that bound not only knowledge of the particle number ratio is necessary but also knowledge of the position of the particles of each batch. Accordingly, after deposition of each batch images are taken to determine the spatial position of each particle of one batch at the surface of the microarray.

Figure 7A:
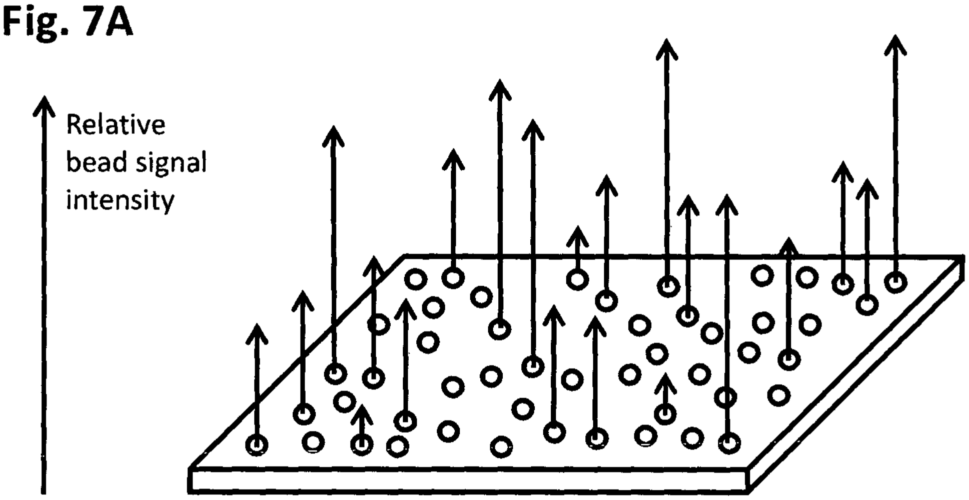
FIG. 7 shows a microarray in Fig A with bead signal intensities arising from the binding of an analyte to beads and a histogram in Fig B plotting particle count versus signal intensity.
Figure 7B:
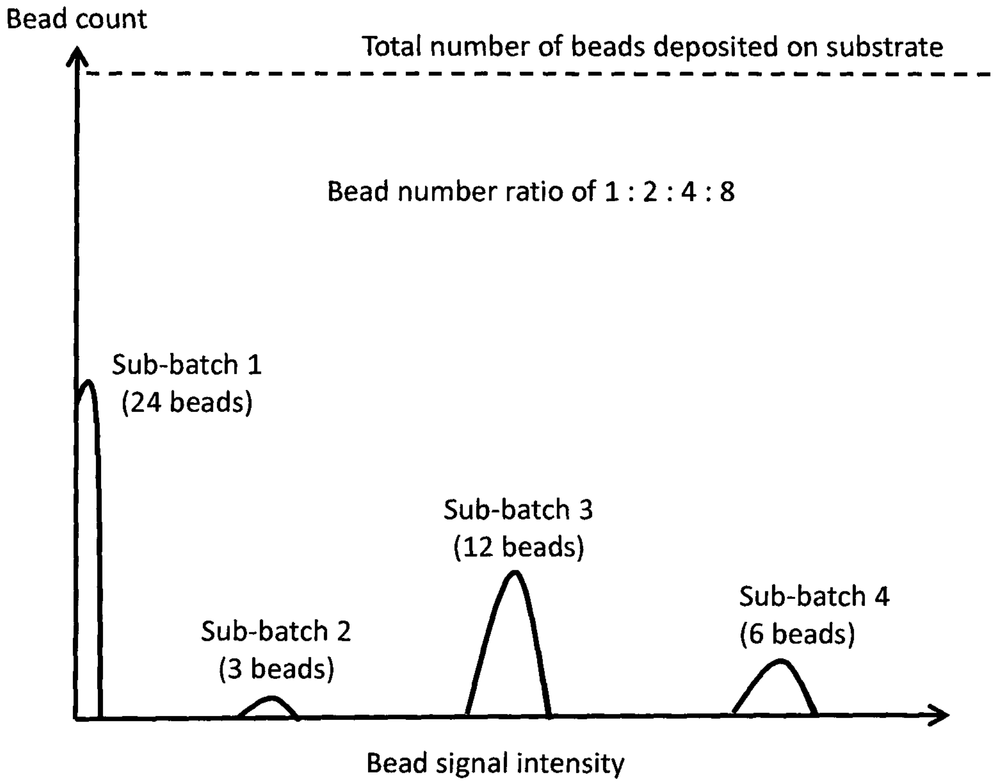

FIG. 7A shows a microarray which was formed by a batch formed of 4 sub-batches with predefined and known bead number ratios of 1:2:4:8 without employing any physical tags or labels on beads. After analyte incubation any means can be employed to generate a signal from beads that have bound its respective analyte. The signal intensities generated by beads are presented as arrows with different length according to the signal intensities. As illustrated in FIG. 7A, four sub-bead batches are present of which one is not generating a signal and three generating a signal of different intensity indicated by the arrows. The differences in intensity are caused either because different analyte concentrations were present in the sample or different sub-batches have a different sensitivity and the same analyte concentration was present or mixtures thereof. FIG. 7B is showing a histogram of the microarray of FIG. 7A plotting particle count or number versus signal intensity. By using such a plot or analyzing particle numbers and signal intensities all beads of all sub-batches can be identified on the microarray. FIG. 7B shows a plurality of beads with a relative particle number of 8 (compared to other pluralities) having a signal intensity close to or zero (0); enabling the identification of this sub-batch and its correlated analyte and concluding no analyte was present as the signal intensity is zero. Three (3) sub-batch populations are visible in the histogram with increasing signal intensities and a relative particle count of 1:4:2 respectively. As signals are observed in these three populations the analyte was present in the sample. The quantification of the analyte is possible by performing a calibration; e.g. by measuring several standards of the analyte and correlate the signal intensity to the analyte concentration. As it can be seen from the disclosed FIG. 7, the decoding can be performed by analyzing relative signal intensities and determining the respective bead numbers without knowing the analyte concentrations. In this way a qualitative analysis of the presents or absence (yes or No) of the analytes can be performed. To determine quantitative analyte concentrations a calibration can be performed. Methods for measuring quantitative analyte concentrations are known in the art.

EXAMPLES

Non-limiting examples of the invention and a comparative example will be further described in greater detail by reference to specific Examples, which should not be construed as in any way limiting the scope of the invention.

Example 1

Combination Method 1 (Single Deposition and Single Reagent Incubation

This example demonstrates the use of 5 sub-batches of different bead ratio to encode 5 different beads (or target analytes) with a single bead deposition and reagent incubation.

In a first step, Batch "M" is formed by mixing sub-batches of different bead ratios as shown below in Table 2.

TABLE 2

Bead number ratios used for combination method 1

| Batch | Bead Ratios | Total beads deposited | Beads in sub-batches |
|---|---|---|---|
| M | 16/8/4/2/1 | 31000 | 16000/8000/4000/2000/1000 |

Next, batch M was deposited onto a substrate in a single deposition step to form a microarray. The microarray was then incubated with the sample. Next, the microarray was incubated with reagent "R". The microarray was then imaged and the bead signals were analysed. As each of the 5 analytes is associated with a specific bead number ratio, the identity of the analytes which are present in the sample could be determined from the total bead signal strength. For example, if a total bead signal equivalent to 3000 beads is obtained, this indicates that the analytes associated with bead number ratios 1 and 2 are present in the sample (since 3000=1000+2000). All 5 different target analytes could thus be decoded using the above method.

Example 1-1

Proof of Concept Experiment

Three kinds of microbeads coated respectively with anti-PSA antibody (bead batch A), anti-hCG antibody (bead batch B) and oligonucleotide probe (bead batch C) were mixed together. Three different batches of beads to detect target analytes A, B and C are prepared with a bead number of 2575 beads/microliter, 1900 beads/microliter and 2300 beads/microliter for A, B and C respectively. The batches are then mixed using equal volumes with no dilution for A, a 3.7× dilution for B and a 22.3× dilution for C resulting in a relative bead ratio of 2575:515:103 or 100:20:4 for A:B:C.

The beads are then randomly deposited on a microarray substrate based on gel pads. Sample solutions which contained (1) only PSA (i.e. only target analyte A); (2) only hCG (i.e. only target analyte B); (3) only target oligonucleotide (i.e. only target analyte C); (4) both PSA and hCG (i.e. target analytes A and B); (5) both PSA and target oligonucleotide (i.e. target analytes A and C); (6) both hCG and target oligonucleotide (i.e. target analytes B and C) are applied and incubated for 1 hour followed by washing with PBS. The fluorescence labeled (FITC) detection antibodies were applied onto the array and incubate for 1 hour followed by washing of unbound antibody conjugate with PBS buffer. The arrays were imaged using a fluorescence microscope. The number of all microbeads and fluorescent microbeads was then counted and the ratio of total beads to detected bead (beads binding the analyte) is calculated.

The results are illustrated in FIGS. 4A to 4F and the quantitative data is presented in the following table.

TABLE 3

Results of proof of concept experiment

| Analyte(s) | No. of Detected beads | Total no. of beads | Actual % of beads detected | Expected theoretical % | % accuracy |
|---|---|---|---|---|---|
| A | 181 | 231 | 78.4 | 80.6 | 97.2 |
| B | 39 | 225 | 17.3 | 16.1 | 94.2% |
| C | 9 | 336 | 2.7 | 3.2 | 84.4% |
| A and B | 247 | 267 | 92.5 | 96.8 | 95.5 |
| A and C | 185 | 219 | 84.5 | 83.9 | 99.2% |
| B and C | 40 | 241 | 16.7 | 19.4 | 86.1% |

The results show a close correlation between the theoretical expected number of beads to be detected for each target analyte and the actual number of beads detected, thereby illustrating the workability of the method.

Hence, this example clearly demonstrates that a microarray comprising particles without a physical tag can be successfully decoded by means of a single deposition of particles, the use of a single reagent and different bead ratios associated with each target analyte.

Example 2

Combination Method 2 (Multiple Depositions and Single Reagent Incubation)

This example demonstrates the use of 3 batches, each containing sub-batches of different bead number ratios to encode 15 different beads (or target analytes) using multiple bead depositions and a single reagent incubation.

In a first step, batches M1, M2 and M3 were formed by mixing sub-batches of different bead number ratios as shown below in Table 4.

TABLE 4

Bead number ratios used in combination method 2

| Batch | Ratio | Total beads deposited | Beads in sub-batches |
|---|---|---|---|
| M1 | 16/8/4/2/1 | 31000 | 16000/8000/4000/2000/1000 |
| M2 | 16/8/4/2/1 | 31000 | 16000/8000/4000/2000/1000 |
| M3 | 16/8/4/2/1 | 31000 | 16000/8000/4000/2000/1000 |

Next, batches M1, M2 and M3 were sequentially deposited onto the substrate. After each batch was deposited, the substrate was imaged. After the microarray was completely fabricated, the microarray was incubated with the sample. Next, the microarray was incubated with reagent "R". The microarray was then imaged and the bead signals were analysed.

The spatial location of each batch was determined by comparison of the three images obtained earlier during the microarray fabrication process. Hence, the identity of each batch could be determined. The identity of each target analyte (sub-batch) within each batch was then decoded by using the specific bead number ratios associated with each target analyte.

Using the above method, all 15 different target analytes could be decoded.

This example demonstrates that a microarray comprising particles without a physical tag can be successfully decoded by means of multiple depositions of particles with images made after each deposition, the use of a single reagent and different bead ratios associated with each target analyte.

Example 3

Combination Method 3 (Single Deposition of a Super Batch and Multiple Reagent Incubations)

This example demonstrates the use of a super batch containing 3 batches, each of which contains 5 sub-batches of different bead number ratios to encode 15 different beads (or target analytes) using a single deposition step and multiple reagent incubations.

In a first step, a super batch was formed by mixing batches M1, M2 and M3. Each batch contained sub-batches of different bead ratios as shown below in Table 5.

TABLE 5

Bead number ratios used in combination method 3

| Batch | Ratio | Total beads deposited | Beads in sub-batches |
|---|---|---|---|
| M1 | 16/8/4/2/1 | 31000 | 16000/8000/4000/2000/1000 |
| M2 | 16/8/4/2/1 | 31000 | 16000/8000/4000/2000/1000 |
| M3 | 16/8/4/2/1 | 31000 | 16000/8000/4000/2000/1000 |

Next, the super batch was deposited onto a substrate in a single deposition step to fabricate the microarray. The completed microarray was then imaged. Hence, there is no separate imaging after each batch was deposited. Next, the microarray was incubated with the sample.

After this, the microarray was incubated with reagent "R1" which contains all the reagents necessary for detecting all the sub-batches within batch M1. The bead signals were then analysed and the target analytes within batch M1 were identified based on the specific bead number ratio associated with each target analyte.

The microarray was then incubated with reagent "R2" which contains all the reagents necessary for detecting all the sub-batches within batch M2. The bead signals were then analysed as before in order to identify the different analytes within batch M2.

Finally, the microarray was incubated with reagent "R3" which contains all the reagents necessary for detecting all the sub-batches within batch M3. The bead signals were then analysed as before in order to identify the different target analytes within batch M3.

Using the above method, all 15 different target analytes could be decoded.

This example demonstrates that a microarray comprising particles without a physical tag can be successfully decoded by means of single deposition of particles, the use of a multiple reagents sequentially applied and different bead ratios associated with each target analyte.

Example 4

Combination Method 4 (Multiple Depositions and Multiple Reagent Incubations)

This example demonstrates the use of 3 batches, each containing sub-batches with the same bead number ratios to encode 15 different beads (or analytes) using multiple bead depositions and multiple reagent incubations.

In a first step, batches M1, M2 and M3 were formed by mixing sub-batches with the same bead number ratios, as shown below in Table 6.

TABLE 6

Bead number ratios in combination method 4

| Batch | Ratio | Total beads deposited | Beads in sub-batches (A/B/C/D/E) |
|---|---|---|---|
| M1 | 1/1/1/1/1 | 50000 | 1000/1000/1000/1000/1000 |
| M2 | 1/1/1/1/1 | 50000 | 1000/1000/1000/1000/1000 |
| M3 | 1/1/1/1/1 | 50000 | 1000/1000/1000/1000/1000 |

Next, batches M1, M2 and M3 were sequentially deposited onto the substrate. After each batch was deposited, the substrate was imaged. After the microarray was completely fabricated, the microarray was incubated with the sample.

Next, the microarray was incubated with reagent "R-a" which contains all the reagents necessary for detecting sub-batch A of batches M1, M2 and M3. The bead signals were then analysed and the identities of the different analytes (sub-batches) was determined based on the known spatial locations of each batch.

The microarray was then incubated with reagent "R-b" which contains all the reagents necessary for detecting sub-batch B of batches M1, M2 and M3. The bead signals were then analysed and the identities of the different analytes (sub-batches) was determined based on the known spatial locations of each batch.

The above process was repeated another three times using reagents "R-c", "R-d" and "R-e", each of which are specific for sub-batches C, D and E respectively of batches M1, M2 and M3.

In this fashion, all 15 different analytes could be decoded.

This example demonstrates that a microarray comprising particles without a physical tag can be successfully decoded by means of single deposition of particles, the use of multiple reagents sequentially applied and different bead ratios associated with each target analyte.

Example 5

Multiple Panel Microarray

This example demonstrates the use of the method of the present disclosure for encoding and decoding a microarray containing 3 different analyte panels, for example, a cancer panel, a cytokine panel and an infectious disease panel. Each panel is able to detect 7 different analytes. The cytokine panel for example is able to detect INFgamma, TNFalpha, GMCSF, IL1alpha, IL1beta, IL2 and IL4.

Using combination method 4 as described in Example 4, 7 batches, each containing 3 sub-batches (one from each panel) with the same bead number ratio, were sequentially deposited on the substrate. Images of the substrate were taken after each batch was deposited.

Table 7 below shows the bead number ratios of each batch used. Sub-batch A (shown in bold) in all 7 batches (M1 to M7) is specific for the cytokine panel. The particular analytes associated with each sub-batch is also indicated.

TABLE 7

Bead number ratios used in multiple panel array

| Batch | Bead Ratios | Total beads deposited | Beads in sub-batches (A/B/C) |
|---|---|---|---|
| M1 | 1/1/1 | 3000 | **1000 (INFgamma)**/1000/1000 |
| M2 | 1/1/1 | 3000 | **1000 (TNFalpha)**/1000/1000 |
| M3 | 1/1/1 | 3000 | **1000 (GMCSF)**/1000/1000 |
| M4 | 1/1/1 | 3000 | **1000 (IL1alpha)**/1000/1000 |
| M5 | 1/1/1 | 3000 | **1000 (IL1beta)**/1000/1000 |
| M6 | 1/1/1 | 3000 | **1000 (IL2)**/1000/1000 |
| M7 | 1/1/1 | 3000 | **10004)**/1000/1000 |

To use the multi panel microarray, the microarray is first incubated with the sample of interest. Next, the end-user selects the panel he/she is interested in. Each panel is specific for a different reagent set. For example, reagent set "R-a" contains the reagents necessary for analyzing the cytokine panel. Thus, if the user wishes to analyse the sample for the 7 cytokine analytes of the cytokine panel, the microarray is incubated with reagent set "R-a" and then the bead signals are analysed. The identities of each of the 7 cytokine analytes can then be determined based on the known spatial locations of each sub-batch.

If the user subsequently wishes to analyse the sample for the cancer panel, he/she could then incubate the microarray with the reagent set specific for the cancer panel and decode the 7 cancer analytes based on the spatial locations of each sub-batch. Hence, by using the described method, a multiple panel microarray capable of analyzing 21 different analytes can be produced with only 7 sequential deposition steps. In addition, such a multiple panel microarray allows the end-user the flexibility of choosing which panel he/she wishes to analyse by simply incubating the microarray with the appropriate reagent set.

There is no real limitation to the number of panels that could be included on a substrate. Hence, the disclosed method can be used to produce a generic chip encoding hundreds of panels with thousands of analytes using only a small number of manufacturing steps.

Example 6

Pooling Method for Reducing Number of Deposition Steps Needed to Manufacture Microarray The following demonstrates a non limiting example of the combinatory encoding method of the present invention using a pooling approach in order to reduce the number of deposition steps necessary for manufacturing a microarray of the present invention.

In table 8 shown below, 104 sub-batches, each specific for a different target analyte (i.e. there are 104 target analytes in this example) are encoded by using only 13 batches.

TABLE 8

Example of Pooling Strategy

| | Total no. of beads present in each batch | | | | | | | | | | | | | Total no. |
|---|---|---|---|---|---|---|---|---|---|---|---|---|---|---|
| | 29 | 29 | 29 | 29 | 28 | 19 | 19 | 19 | 19 | 19 | 19 | 19 | 19 | of beads |
| | Batch no. | | | | | | | | | | | | | used per |
| Sub-batch No. | 1 | 2 | 3 | 4 | 5 | 6 | 7 | 8 | 9 | 10 | 11 | 12 | 13 | sub-batch |
| 1 | 1 | | | | | 1 | | | | | | | | 2 |
| 2 | | 1 | | | | | 1 | | | | | | | 2 |
| 3 | | | 1 | | | | | 1 | | | | | | 2 |
| 4 | | | | 1 | | | | | 1 | | | | | 2 |
| 5 | | | | | 1 | | | | | 1 | | | | 2 |
| 6 | 1 | | | | | | | | | | 1 | | | 2 |
| 7 | | 1 | | | | | | | | | | 1 | | 2 |
| 8 | | | 1 | | | | | | | | | | 1 | 2 |
| 9 | | | | 1 | | 1 | | | | | | | | 2 |
| 10 | | | | | 1 | | 1 | | | | | | | 2 |
| 11 | 1 | | | | | | | 1 | | | | | | 2 |
| 12 | | 1 | | | | | | | 1 | | | | | 2 |
| 13 | | | 1 | | | | | | | 1 | | | | 2 |
| 14 | | | | 1 | | | | | | | 1 | | | 2 |
| 15 | | | | | 1 | | | | | | | 1 | | 2 |
| 16 | 1 | | | | | | | | | | | | 1 | 2 |
| 17 | | 1 | | | | 1 | | | | | | | | 2 |
| 18 | | | 1 | | | | 1 | | | | | | | 2 |
| 19 | | | | 1 | | | | 1 | | | | | | 2 |
| 20 | | | | | 1 | | | | 1 | | | | | 2 |
| 21 | 1 | | | | | | | | | 1 | | | | 2 |
| 22 | | 1 | | | | | | | | | 1 | | | 2 |
| 23 | | | 1 | | | | | | | | | 1 | | 2 |
| 24 | | | | 1 | | | | | | | | | 1 | 2 |
| 25 | | | | | 1 | 1 | | | | | | | | 2 |
| 26 | 1 | | | | | | 1 | | | | | | | 2 |
| 27 | | 1 | | | | | | 1 | | | | | | 2 |
| 28 | | | 1 | | | | | | 1 | | | | | 2 |
| 29 | | | | 1 | | | | | | 1 | | | | 2 |
| 30 | | | | | | 1 | | | | | 1 | | | 2 |
| 31 | 1 | | | | | | | | | | | 1 | | 2 |
| 32 | | 1 | | | | | | | | | | | 1 | 2 |
| 33 | | | 1 | | | 1 | | | | | | | | 2 |
| 34 | | | | 1 | | | 1 | | | | | | | 2 |
| 35 | | | | | 1 | | | 1 | | | | | | 2 |
| 36 | 1 | | | | | | | | 1 | | | | | 2 |
| 37 | | 1 | | | | | | | | 1 | | | | 2 |
| 38 | | | 1 | | | | | | | | 1 | | | 2 |
| 39 | | | | 1 | | | | | | | | 1 | | 2 |
| 40 | | | | | 1 | | | | | | | | 1 | 2 |
| 41 | 2 | | | | | 1 | | | | | | | | 3 |
| 42 | | 2 | | | | | 1 | | | | | | | 3 |
| 43 | | | 2 | | | | | 1 | | | | | | 3 |
| 44 | | | | 2 | | | | | 1 | | | | | 3 |
| 45 | | | | | 2 | | | | | 1 | | | | 3 |
| 46 | 2 | | | | | | | | | | 1 | | | 3 |
| 47 | | 2 | | | | | | | | | | 1 | | 3 |
| 48 | | | 2 | | | | | | | | | | 1 | 3 |
| 49 | | | | 2 | | 1 | | | | | | | | 3 |
| 50 | | | | | 2 | | 1 | | | | | | | 3 |
| 51 | 2 | | | | | | | 1 | | | | | | 3 |
| 52 | | 2 | | | | | | | 1 | | | | | 3 |
| 53 | | | 2 | | | | | | | 1 | | | | 3 |
| 54 | | | | 2 | | | | | | | 1 | | | 3 |
| 55 | | | | | 2 | | | | | | | 1 | | 3 |
| 56 | 2 | | | | | | | | | | | | 1 | 3 |
| 57 | | 2 | | | | 1 | | | | | | | | 3 |
| 58 | | | 2 | | | | 1 | | | | | | | 3 |
| 59 | | | | 2 | | | | 1 | | | | | | 3 |
| 60 | | | | | 2 | | | | 1 | | | | | 3 |
| 61 | 2 | | | | | | | | | 1 | | | | 3 |
| 62 | | 2 | | | | | | | | | 1 | | | 3 |
| 63 | | | 2 | | | | | | | | | 1 | | 3 |
| 64 | | | | 2 | | | | | | | | | 1 | 3 |
| 65 | | | | | 2 | 1 | | | | | | | | 3 |
| 66 | 2 | | | | | | 1 | | | | | | | 3 |
| 67 | | 2 | | | | | | 1 | | | | | | 3 |
| 68 | | | 2 | | | | | | 1 | | | | | 3 |
| 69 | | | | 2 | | | | | | 1 | | | | 3 |
| 70 | | | | | 2 | | | | | | 1 | | | 3 |
| 71 | 2 | | | | | | | | | | | 1 | | 3 |

TABLE 8-continued

Example of Pooling Strategy

| | Total no. of beads present in each batch | | | | | | | | | | | | | Total no. |
|---|---|---|---|---|---|---|---|---|---|---|---|---|---|---|
| | 29 | 29 | 29 | 29 | 28 | 19 | 19 | 19 | 19 | 19 | 19 | 19 | 19 | of beads |
| | Batch no. | | | | | | | | | | | | | used per |
| Sub-batch No. | 1 | 2 | 3 | 4 | 5 | 6 | 7 | 8 | 9 | 10 | 11 | 12 | 13 | sub-batch |
| 72 | | 2 | | | | | | | | | | | 1 | 3 |
| 73 | | | 2 | | | 1 | | | | | | | | 3 |
| 74 | | | | 2 | | | 1 | | | | | | | 3 |
| 75 | | | | | 2 | | | 1 | | | | | | 3 |
| 76 | 2 | | | | | | | | 1 | | | | | 3 |
| 77 | | 2 | | | | | | | | 1 | | | | 3 |
| 78 | | | 2 | | | | | | | | 1 | | | 3 |
| 79 | | | | 2 | | | | | | | | 1 | | 3 |
| 80 | | | | | 2 | | | | | | | | 1 | 3 |
| 81 | 1 | | | | | 3 | | | | | | | | 4 |
| 82 | | 1 | | | | | 3 | | | | | | | 4 |
| 83 | | | 1 | | | | | 3 | | | | | | 4 |
| 84 | | | | 1 | | | | | 3 | | | | | 4 |
| 85 | | | | | 1 | | | | | 3 | | | | 4 |
| 86 | 1 | | | | | | | | | | 3 | | | 4 |
| 87 | | 1 | | | | | | | | | | 3 | | 4 |
| 88 | | | 1 | | | | | | | | | | 3 | 4 |
| 89 | | | | 1 | | 3 | | | | | | | | 4 |
| 90 | | | | | 1 | | 3 | | | | | | | 4 |
| 91 | 1 | | | | | | | 3 | | | | | | 4 |
| 92 | | 1 | | | | | | | 3 | | | | | 4 |
| 93 | | | 1 | | | | | | | 3 | | | | 4 |
| 94 | | | | 1 | | | | | | | 3 | | | 4 |
| 95 | | | | | 1 | | | | | | | 3 | | 4 |
| 96 | 1 | | | | | | | | | | | | 3 | 4 |
| 97 | | 1 | | | | 3 | | | | | | | | 4 |
| 98 | | | 1 | | | | 3 | | | | | | | 4 |
| 99 | | | | 1 | | | | 3 | | | | | | 4 |
| 100 | | | | | 1 | | | | 3 | | | | | 4 |
| 101 | 1 | | | | | | | | | 3 | | | | 4 |
| 102 | | 1 | | | | | | | | | 3 | | | 4 |
| 103 | | | 1 | | | | | | | | | 3 | | 4 |
| 104 | | | | 1 | | | | | | | | | 3 | 4 |

The 104 sub-batches are mixed into 13 batches according to table 6, wherein the numbers indicate the relative bead ratios. For example, sub-batch number 1 is present in batches nos. 1 and 6 with a relative bead ratio of 1. Sub-batch 41 is present in batch No. 1 with a bead ratio of 2 and present in batch no. 6 with a ratio of 1 and so on. By using a combination of sub-batches in different batches with different relative bead ratios all 104 sub-batches are encoded in 13 batches. An image is made after each batch is sequentially deposited on the substrate. The microarray created using this method is then used in the following fashion.

The microarray is first incubated with the sample. After this, the microarray is incubated with a single reagent which allows detection of all of the target analytes. An image of the beads emitting an optical signal can then be captured.

Next, the batch from which a bead originates can be determined by comparing the images made during the deposition process as described in the preceding combination methods.

The user can then identify the specific sub-batch and therefore target analytes present, based on the principle that each and every bead batch is present in exactly 2 different pools in the present example. So if sub-batch no. 1 (i.e. target analyte no. 1) is present in the sample, an optical signal will be obtained for both batch nos. 1 and 6. Also, if for instance a signal is only obtained in batch 1 but no signal is obtained for batch no. 6, it follows that bead batch no. 1 cannot be present in the sample.

To further illustrate how the pooling method works, suppose for instance that an optical signal is only obtained for batch nos. 1 and 6. In this case, any one of the following three scenarios could apply:

(a) The optical signal originates from both sub-batch nos. 1 and 41.

(b) The optical signal originates from only sub-batch no. 1.

(c) The optical signal originates from only sub-batch no. 41.

In order to determine which scenario is correct, the different bead ratios are used. In batch no. 1, sub-batch no. 1 has a bead number ratio of 1 whereas sub-batch no. 44 has a bead number ratio of 2. Hence, if for example a total bead signal of 3 is obtained, it would indicate that scenario (a) is correct. Conversely, if a total bead signal of 2 is obtained, this would indicate that scenario (c) is correct.

Accordingly, a unique combination of signals will be obtained depending on the target analytes present and the identities of the target analytes present can be determined unambiguously as described above.

This example is for illustration only and is a non limiting example—any other combination of batches and ratios is possible to decode a smaller or much larger number of sub-batches (and therefore a smaller or much larger number of target analytes). The present invention using a pooling approach solves the problem of reducing the manufacturing time of bead microarrays which rely on sequential bead deposition. Instead of depositing 104 bead batches sequentially, only 13 bead pooled batches are deposited which include the bead identity information. This leads to a dramatic reduction in manufacturing time and cost.

Guidelines for Developing Layout Table for Pooling

The following non-limiting example provides rules and guidelines on how to design a pooling strategy for the combinatory encoding method of the current invention. In the following, "B" means the batch number (columns), "SB" means the sub-batch number (rows), "F" means the factor normalized to 1 (one) for the bead ratio in different pools. The term (SB:B) with "SB" and "B" as integer numbers refers to a specified position in the pooling table. For example, (5:2) refers to sub-batch No. 5. and batch No. 2

A non limiting example of a pooling table is shown in Table 8. The guidelines for generating such a table are as follows.

At any given position in the pooling table a bead sub-batch may or may not be present.

If a bead sub-batch is present, the sub-batch can have any given bead ratio dictated by the factor "F" (e.g. beads per volume) compared to other sub-batches in the pooling table. The bead ratio can be any number, integer or non-integer.

"n" indicates the frequency at which a bead sub-batch is present in a batch. For example, a bead sub-batch with n=5 is present in every $5^{th}$ batch, whilst a bead sub-batch with n=1 means that the bead sub-batch is present in every batch.

In order to eventually be able to distinguish two sub-batches from each other, the factors "F" from both batches must not be equal throughout all positions "B". For example, for bead sub-batches 7 and 38 in Table 6, there must be at least one value "F" for either (7:B) or (38:B) wherein "F" for the same batch number is different, i.e. there must be at least one batch where "F" is different between bead sub-batches 7 and 38.

To improve the robustness of the encoding/decoding, a larger number of different "F" values can be used. There is no theoretical limit for the number of positions at which "F" is different. Accordingly, for a given number of sub-batches and batches, an infinite number of different combinations can potentially exist, because "F" at all positions (SB:B) could have any value. Hence, there is a potentially infinite number of combinations related to an infinite number of solutions for a given combinatory encoding problem. That said, in a preferred pooling strategy, all of the batches would have a similar number of total beads and differences in the Factor "F" between positions (SB:B) in the pooling table would be kept low so as to minimize the number of beads required, but yet large enough to distinguish different ratios.

By applying the above rules a large number of sub-batches can be encoded by using a small number of batches, thereby reducing the number of deposition steps required. By using fewer batches for a given number of sub-batches, a larger number of different bead ratios are required for encoding. Conversely, when more batches are used, a fewer number of bead ratios is required.

A preferred pooling strategy would employ a limited number of bead ratios, for example, but not limited to, the ratios of 1:2:4:8 with an "F" factor of at least two (2) between different sub-batches to clearly distinguish between those different sub-batches. The maximum bead ratio difference in this non-limiting example is eight (8) which avoids extreme differences of bead numbers in different sub-batches.

A batch could also contain no beads of a particular sub-batch resulting in a ratio of 0:1:2:4:8. Although using no beads can reduce the number of beads required, the drawback is that it reduces the potential number of combinations that can be encoded. For example, if only two batches were used, although 32 (2^5) different combinations could exist, because the combination of zero beads in both batches does not provide analytical information, there is only a total of 31 useful combinations.

In this example, a clear and simple decoding of a sample containing only one analyte is possible. For samples with more than one analyte, the total number of beads in both batches must be different to an extent that the bead ratios can be determined. For samples with more than one analyte a larger number of batches are preferred so as to create larger differences in the total number of beads in different batches and less combinations that lead to similar bead numbers or numbers close to each other.

Applications

Advantageously, the method of the present disclosure provides an improved method for making bead microarrays that do not require a physical identifier or tag on beads. More advantageously, such bead microarrays with multiplexing capability can be fabricated with a single bead deposition step greatly reducing time and cost of manufacturing.

The method of the present disclosure may also be combined with state-of-the art microarray methods to substantially improve the performance of such known methods.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method of encoding a microarray, the method comprising: depositing a first batch of particles on a substrate, the first batch of particles comprising at least two sub-batches of the particles, each of the sub-batches being capable of binding to a different, specific target analyte, wherein the at least two sub-batches are deposited as a mixture; and providing, prior to or during the depositing, information necessary for decoding the microarray, the information including a unique particle number ratio of the sub-batches to each other.

2. The method according to claim 1, further comprising decoding the microarray by:

analyzing an image of the microarray obtained after contacting the microarray with a sample; wherein analyzing of the image comprises:

(i) determining a total number of the particles and a number of detectable signals obtained from binding of one of the target analytes to one of the sub-batches of particles deposited on the microarray; and (ii) decoding information obtained under sub-step (i) using the particle number ratio of the sub-batches.

3. The method according to claim 1, further comprising, after depositing the first batch of particles, taking an image of the first batch of particles so as to provide information about a position of the particles in the first batch of particles.

4. The method according to claim 3, further comprising decoding the microarray by:

analyzing an image of the microarmy obtained after contacting the microarray with a sample; wherein analyzing of the image comprises:

(i) determining a position and number or intensity of detectable signals obtained from binding of one of the target analytes to one of the sub-hatches of particles deposited on the microarray; and (ii) decoding information obtained under sub-step (i) using the information about the position of the particles and the particle number ratio of the sub-batches.

5. The method according to claim 3, further comprising sequentially repeating the depositing and imaging steps with subsequent batches of the particles each having at least two sub-batches of particles, wherein, in each case, particle number ratios of the sub-batches are known, the subsequent batches each being configured to bind to one or more different, specific target analytes than the first batch of particles.

6. The method according to claim 5, further comprising decoding the microarray using the information about the position of the particles in the respective batches and the known particle number ratios of the sub-batches.

7. The method according to claim 5, further comprising decoding the microarray by:

analyzing an image of the microarray obtained after contacting the microarray with a sample; wherein analyzing of the image comprises:

(i)determining a position and number or intensity of detectable signals obtained from binding of one of the target analytes to one of the sub-batches of particles deposited on the microarray; and (ii) decoding information obtained under sub-step (i) using the information about the position of the particles and the particle number ratios of the sub-batches.

8. The method according to claim 5, wherein the known particle number ratios of the subsequent batches are different from each other and different from the known particle number ratio of the first batch of particles.

9. The method according to claim 8, further comprising decoding the microray using the information about the position of the particles in the respective batches and the different known particle number ratios of the sub-batches.

10. The method according to claim 3, wherein a second batch of the particles subsequent to the first batch has a different particle number ratio of the sub-batches than the first batch.

11. The method according to claim 1, wherein the particle number ratio is between 100/1 and 1/1.

12. The method according to claim 11, wherein the particle number ratio is between 11/1 and 1/1.

13. The method according to claim 1, wherein the particle number ratio is a prime number.

14. The method according to claim 1, wherein the particles are selected from a group consisting of microbeads and biological entities.

15. The method according to claim 14, wherein the particles include microbeads and the microbeads have a shape selected from the group consisting of a microsphere, a microcapsule, a microrod, a microcube and a microtube.

16. The method according to claim 15, wherein the microbeads are formed of a material selected from the group consisting of plastic, ceramic, glass, metal, a metal oxide, silicon dioxide, polystyrene, methylstyrene, acrylic polymer, sepharose, cellulose, nylon, cross-linked micelles, Teflon, paramagnetic material, thoria sol, carbon graphite, titanium dioxide, latex, a cross-linked dextran, and compositions used in peptide, nucleic acid and organic moiety synthesis or mixtures thereof.

17. The method according to claim 14, wherein the particles include the biological entities and the biological entities are selected from the group consisting of a cell, a bacterium, or a virus particle.

18. The method according to claim 1, wherein the particles are of a size of 0.1to 500 μm, or 0.1 to 200 μm, or 0.1 μm to 100 μm, or 1 to 100 μm, or 1 to 10 μm.

19. The method according to claim 1, wherein the particles are tagged with an identifier.

20. The method according to claim 19, wherein the identifier is selected from a group consisting of a fluorescent tag, a bar code, a chemical identifier, a quantum dot, a microstructure, a nucleic acid identifier, an engraving and a radio frequency tag.

21. The method according to claim 1, further comprising decoding the microarray using the particle number ratio.

22. The method according to claim 1, further comprising decoding the microarray by:

analyzing an image of the microarray obtained after contacting the microarray with a sample; wherein analyzing of the image comprises:

(i) determining a total number of particles, and (ii) determining a number of particles from which signals of similar intensity are obtained from binding of one of the target analytes to one of the sub-batches; and decoding the microarray by calculating a number ratio from information obtained under sub-step (i) and (ii) and comparing the number ratio with the unique particle number ratio of the sub-hatches used for deposition of the particles to identify the target analytes bound to the particles of the microarray.

23. A method of manufacturing a microarray, comprising: i) providing at least two sub-batches of particles having one or more binding sites thereon, each of the sub-batches being configured to bind with a different, specific target analyte present in a sample, ii) preparing a mixture of the at least two sub-batches of particles, iii) depositing the mixture of particle sub-batches onto a substrate to form the microarray, and iv) providing, prior to or during the depositing, information necessary for decoding the microarray, the information including a unique particle number ratio of the sub-batches to each other.

24. The method according to claim 23, further comprising imaging the substrate having the particles deposited thereon.

25. The method according to claim 23, further comprising sequentially repeating steps i)-iv).

26. The method according to claim 23, wherein the particle number ratio is between 100/1 and 1/1.

27. The method according to claim 26, wherein the the particle number ratio is between 11/1 and 1/1.

28. The method according to claim 23, wherein the particle number ratio is a prime number.

29. The method according to claim 23, wherein the binding sites of the particles of one of the sub-batches bind to only one of the target analytes.

30. The method according to claim 23, wherein each of the particles comprises one or more active agents capable of binding with one or more of the target analytes.

31. The method according to claim 30, wherein the particles comprise at least two active agents that are capable of detecting at least two of the target analytes and a particle number ratio of the sub-batches or active agent binding sites is known and useable to indicate the presence of the at least two or more of the target analytes in the sample.

32. The method according to claim 23, wherein the substrate is selected from the group consisting of polymeric materials, organic materials, inorganic materials, metals, ceramics, plastic, rubber, glass, fibrous materials, graphite or silicon, silicon dioxide, silicon nitride, modified silicon, glass, modified or functionalized glass, inorganic glass, plastics, acrylics, polystyrene, copolymers of styrene, polypropylene, polyethylene, polybutylene, polyurethane, Teflon, polysaccharide, nylon, nitrocellulose, resins, silica, silica-based materials and carbon.

* * * * *